(12) United States Patent
Hilinski

(10) Patent No.: US 11,161,102 B2
(45) Date of Patent: Nov. 2, 2021

(54) IMINIUM SALT ORGANOCATALYSTS, METHOD OF MAKING, AND METHODS OF USING

(71) Applicant: University of Virginia Patent Foundation, Charlottesville, VA (US)

(72) Inventor: Michael Kenneth Hilinski, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 112 days.

(21) Appl. No.: 16/311,475

(22) PCT Filed: Jun. 22, 2017

(86) PCT No.: PCT/US2017/038704
§ 371 (c)(1),
(2) Date: Dec. 19, 2018

(87) PCT Pub. No.: WO2017/223287
PCT Pub. Date: Dec. 28, 2017

(65) Prior Publication Data
US 2019/0344253 A1    Nov. 14, 2019

Related U.S. Application Data

(60) Provisional application No. 62/353,157, filed on Jun. 22, 2016.

(51) Int. Cl.
*B01J 31/02* (2006.01)

(52) U.S. Cl.
CPC ........ *B01J 31/0241* (2013.01); *B01J 2231/70* (2013.01)

(58) Field of Classification Search
None
See application file for complete search history.

(56) References Cited

U.S. PATENT DOCUMENTS

| | | | |
|---|---|---|---|
| 5,360,569 A | * | 11/1994 | Madison .............. C11D 3/3902 510/371 |
| 5,482,515 A | | 1/1996 | Madison et al. |
| 2005/0256017 A1 | | 11/2005 | Dykstra |
| 2009/0221829 A1 | | 9/2009 | Kim et al. |

FOREIGN PATENT DOCUMENTS

| | | |
|---|---|---|
| WO | 2011005730 A1 | 1/2011 |
| WO | 2011127102 A1 | 10/2011 |

OTHER PUBLICATIONS

Finkelstein et al. (Journal of Medicinal Chemistry, 14(7), 584-8 (Year: 1971).*
Heer et al. (Synthetic Communications, 2002, 32(16), 2555-2563 (Year: 2002).*
International Search Report and Written Opinion for PCT/US2017/038704 dated Oct. 10, 2017.

* cited by examiner

*Primary Examiner* — Yun Qian
(74) *Attorney, Agent, or Firm* — Thomas | Horstemeyer, LLP

(57) ABSTRACT

Aspects of the present disclosure include compositions comprising iminium catalyst, methods of making, methods of using, and the like.

5 Claims, 10 Drawing Sheets

Heterocyclic Oxidation Reagents

*C–H Hydroxylation:*

TFDO perfluorinated oxaziridine

*Epoxidation:* oxaziridinium salt

Organocatalytic C–H Hydroxylation

Known: X = O, NR
Unknown: X = $NR_2^+$

Previous Work: Imine and Ketone Catalysts

This Work: Iminium Salt Catalysts

Table 3. Aliphatic hydroxylation of alcohol and ether substrates.[a]

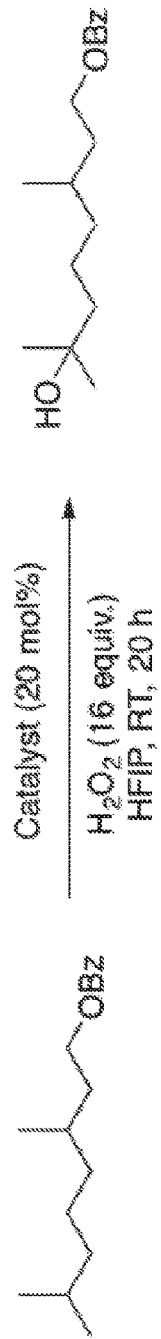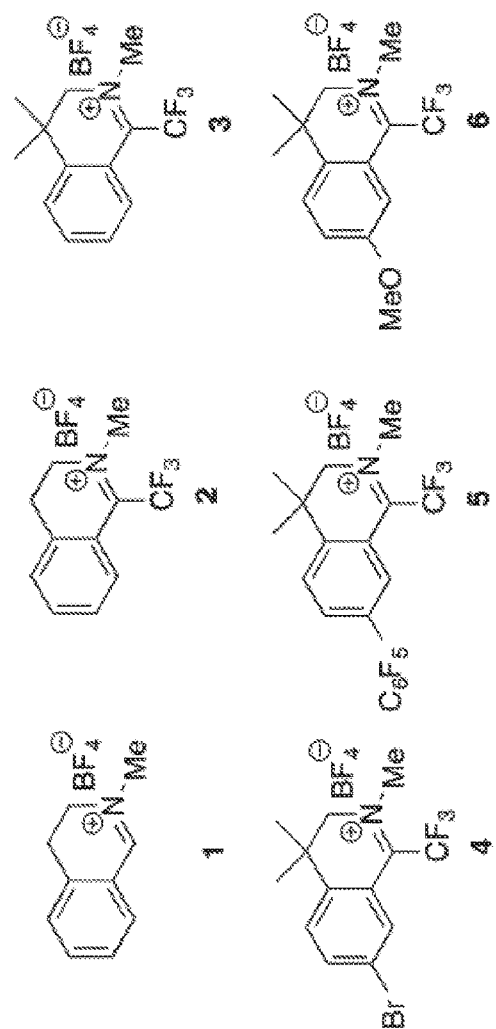
FIG. 5A
FIG. 5B

Activity of 1-8.

| Catalyst | Conversion (%) | Yield (%) |
|---|---|---|
| 1 | <1 | <1 |
| 2 | 12 | 3 |
| 3 | 70 | 57 |
| 4 | 37 | 24 |
| 5 | 35 | 27 |
| 6 | 29 | 20 |
| 7 | — | 37 |
| 8 | — | 48 |

IMINIUM SALT ORGANOCATALYSTS, METHOD OF MAKING, AND METHODS OF USING

CROSS-REFERENCE TO RELATED APPLICATION

This application is the 35 U.S.C. § 371 national stage application of PCT Application No. PCT/US2017/038704, filed Jun. 22, 2017, where the PCT claims the benefit of and priority to U.S. provisional application entitled "AN IMINIUM SALT ORGANOCATALYSTS FOR SELECTIVE ALIPHATIC C-H HYDROXYLATION," having Ser. No. 62/353,157, filed on Jun. 22, 2016, which are entirely incorporated herein by reference.

BACKGROUND

Over the last decade, the development of catalytic methods for site-selective hydroxylation has provided elegant solutions to the problem of discriminating among several potential sites of oxidation on complex molecules. However, there are still considerable challenges preventing the widespread adoption of hydroxylation as a synthetic strategy.

SUMMARY

Aspects of the present disclosure include compositions including an iminium catalyst, methods of making, methods of using, and the like.

In one embodiment, the present disclosure provides generic formula I:

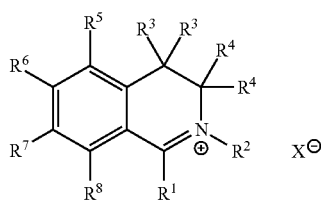

FORMULA I $R^1$ is selected from the group consisting of —H, $C_6F_5$, —$CF_3$, —$CH_2CF_3$, —$CF_2CF_3$, —$CF_2CF_2CF_3$, $C_nF_{n+2}$, alkyl, aryl, fluorinated aryl, cycloalkyl, fluorinated cycloalkyl, —$CO_2R$, $C(O)CO_2R$, where R is any alkyl, alkenyl, alkynyl, or aryl group or substituted versions thereof;

$R^2$ is selected from the group consisting of —$CH_3$, -Ph, —$C_6F_5$, —$CF_3$, —$CH_2Ph$, -cyclohexyl, -adamantyl, -cyclopropyl, —$C_nH_{n+2}$, $C_nF_{n+2}$, biphenyl, substituted biphenyl, alkyl, substituted alkyl, perfluoroalkyl, aryl, perfluroaryl, substituted aryl, or glycosyl;

each $R^3$ is independently selected from the group consisting of —$CH_3$, —$CH_2CH_2$—, -Ph, —$CH_2Ph$, —OR, $COCH_3$, —$CO_2CH_3$, —$C_nH_{n+2}$, $C_n$, $F_{n+2}$, cycloalkyl, substituted cycloalkyl, aryl, or perfluoroaryl, each $R^4$ is independently selected from the group consisting of —$CH_3$, —$CH_2CH_2$—, —F, —$CF_3$, alkyl, substituted alkyl, perfluoroalkyl, cycloalkyl, substituted cycloalkyl, or perfluorocycloalkyl;

$R^5$ is selected from the group consisting of —H, —F, —Cl, —Br, —I, $CF_3$, —$C_6F_5$, —$NO_2$, —$OCH_3$, Ph, -p-$C_6H_4NO_2$, —OH, or alkyl;

$R^6$ is selected from the group consisting of —H, —F, —Cl, —Br, —I, $CF_3$, —$C_6F_5$, —$NO_2$, —$OCH_3$, Ph, -p-$C_6H_4NO_2$, —OH, or alkyl;

$R^7$ is selected from the group consisting of —H, —F, —Cl, —Br, —I, $CF_3$, —$C_6F_5$, —$NO_2$, —$OCH_3$, Ph, -p-$C_6H_4NO_2$, —OH, or alkyl;

$R^8$=—H, —F, —Cl, —Br, —I, $CF_3$, —$C_6F_5$, —$NO_2$, —$OCH_3$, Ph, -p-$C_6H_4NO_2$, $CH_2Ph$, -t-Bu, i-Pr —OH, or alkyl wherein each or any one of each $R^1$-$R^8$ can be optionally substituted;

X=—$BF_4^-$, —$BPh_4^-$, $SbF_6^-$, $PF_6^-$, $ClO_4^-$, —$CF_3CO_2^-$, $CH_3SO_3^-$, $F^-$, $Cl^-$, $Br^-$, $I^-$, tetrakis(3,5-bis(trifluoromethyl)phenyl)borate, —$BR_4$, or a pharmaceutically acceptable salt thereof.

In one aspect, an R can be H or optionally substituted.

In one aspect, the two $R_3$s can be referred to as $R_{3a}$ and $R_{3b}$.

In one aspect, the two $R_4$s can be referred to as $R_{4a}$ and $R_{4b}$.

In one aspect, $R_3$=$R_3$. In one aspect, one $R_3$ is not the same as the other $R_3$.

In one aspect, R4=R4. In one aspect, one R4 is not the same as the other $R_4$.

In one aspect, the substituents of $R_1$, $R_2$, $R_3$, $R_4$, $R_5$, $R_6$, $R_7$, and $R_8$ are selected independently from one another.

In one aspect, the present disclosure provides iminium catalysts of Formula I, wherein said catalyst is not catalyst 3a below. In one aspect, the present disclosure provides iminium catalysts of Formula I, wherein said catalyst is not a known catalyst.

The present application provides compositions and methods for preparing iminium catalysts with the enhanced activity as disclosed herein.

In one aspect, a compound having Formula I is catalyst 3b below. In one aspect, a compound having Formula I is catalyst 3c below.

By varying X in any of the aspects described herein, one can arrive at new catalysts such as catalyst 9 (with the $BPh4^{\ominus}$ moiety).

In one embodiment, the present disclosure provides generic formula II:

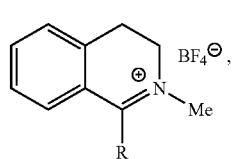

Formula II wherein R is not H and is selected from the group consisting of $C_6F_5$, $CF_3$, $CH_2CF_3$, —$CF_2CF_3$, $CF_2CF_2CF_3$, and $C_nF_{n+2}$.

In another aspect, R is $CF_3$ in a compound of Formula II.

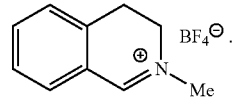

In certain aspects, the iminium catalyst is not

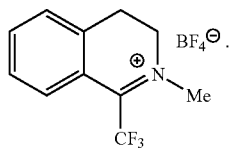

In certain aspects, the iminium catalyst is:

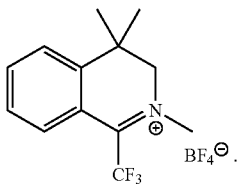

In certain aspects, the iminium catalyst is:
In certain aspects, the iminium catalyst is:

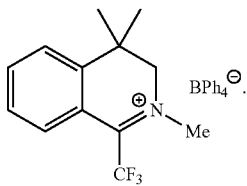 [SMILES: C[N+]1=C(C(F)(F)F)c2ccccc2C(C)(C)C1 ; "BPh4"]

BRIEF DESCRIPTION OF THE DRAWINGS

FIG. 5A illustrates an exemplary reaction scheme that can use catalysts according to the present disclosure.

FIG. 5B illustrates embodiments of catalysts 1-8 as described herein.

FIG. 5C illustrates the activity of catalysts 1-8 of FIG. 5B as used in the reaction of FIG. 5A.

DETAILED DESCRIPTION

Definitions

Figure 1:
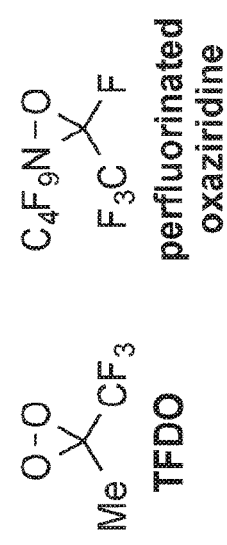
FIG. 1 illustrates the stoichiometric and catalytic C—H oxidation by heterocyclic oxidants and organocatalysts.
Figure 1:
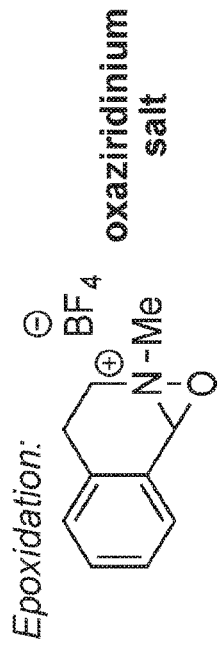
Figure 1:
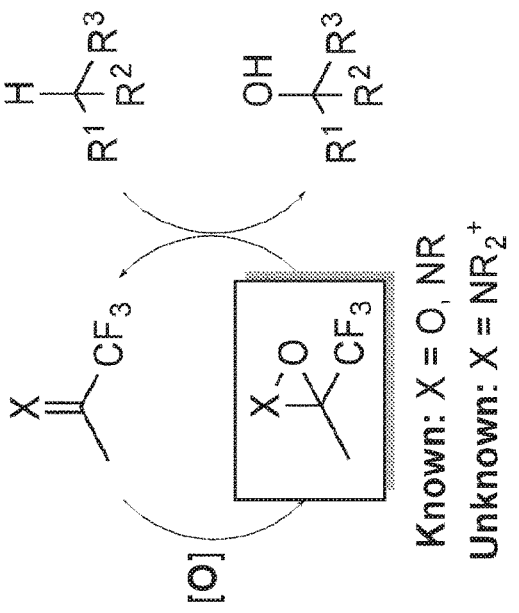
Figure 1:
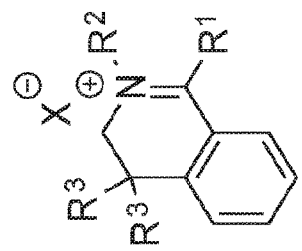
Figure 1:
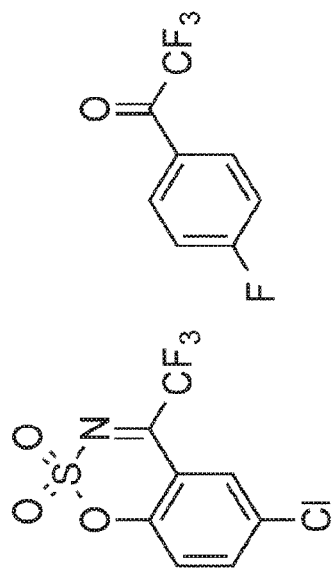

In describing and claiming aspects of the present disclosure, the following terminology will be used in accordance with the definitions set forth below.

The articles "a" and "an" are used herein to refer to one or to more than one (i.e., to at least one) of the grammatical object of the article. By way of example, "an element" means one element or more than one element.

As used herein, an "analog", or "analogue" of a chemical compound is a compound that, by way of example, resembles another in structure but is not necessarily an isomer (e.g., 5-fluorouracil is an analog of thymine).

As used herein, a "derivative" of a compound refers to a chemical compound that may be produced from another compound of similar structure in one or more steps, as in replacement of H by an alkyl, acyl, or amino group.

As used in the specification and the appended claims, the terms "for example," "for instance," "such as," "including" and the like are meant to introduce examples that further clarify more general subject matter. Unless otherwise specified, these examples are provided only as an aid for understanding aspects of the present disclosure, and are not meant to be limiting in any fashion.

The terms "formula" and "structure" are used interchangeably herein. As used herein, a "functional" molecule is a molecule in a form in which it exhibits a property or activity by which it is characterized.

As used herein, "aliphatic" or "aliphatic group" refers to a saturated or unsaturated, linear or branched, cyclic (non-aromatic) or heterocyclic (non-aromatic), hydrocarbon or hydrocarbon group and encompasses alkyl, alkenyl, and alkynyl groups, and alkanes, alkene, and alkynes, for example.

As used herein, "alkane" refers to a saturated aliphatic hydrocarbon which can be straight or branched, having 1 to 40, 1 to 20, 1 to 10, or 1 to 5 carbon atoms, where the stated range of carbon atoms includes each intervening integer individually, as well as sub-ranges. Examples of alkane include, but are not limited to methane, ethane, propane, butane, pentane, and the like. Reference to "alkane" includes unsubstituted and substituted forms of the hydrocarbon.

As used herein, "alkyl" or "alkyl group" refers to a saturated aliphatic hydrocarbon radical which can be straight or branched, having 1 to 40, 1 to 20, 1 to 10, or 1 to 5 carbon atoms, where the stated range of carbon atoms includes each intervening integer individually, as well as sub-ranges. Examples of alkanes include, but are not limited to methyl, ethyl, n-propyl, i-propyl, n-butyl, s-butyl, t-butyl, n-pentyl, and s-pentyl. Reference to "alkyl" or "alkyl group" includes unsubstituted and substituted forms of the hydrocarbon group.

As used herein, "alkene" refers to an aliphatic hydrocarbon which can be straight or branched, containing at least one carbon-carbon double bond, having 2 to 40, 2 to 20, 2 to 10, or 2 to 5 carbon atoms, where the stated range of carbon atoms includes each intervening integer individually, as well as sub-ranges. Examples of alkene groups include, but are not limited to, ethene, propene, and the like. Reference to "alkene" includes unsubstituted and substituted forms of the hydrocarbon.

As used herein, "alkenyl" or "alkenyl group" refers to an aliphatic hydrocarbon radical which can be straight or branched, containing at least one carbon-carbon double bond, having 2 to 40, 2 to 20, 2 to 10, or 2 to 5 carbon atoms, where the stated range of carbon atoms includes each intervening integer individually, as well as sub-ranges. Examples of alkenyl groups include, but are not limited to, ethenyl, propenyl, n-butenyl, i-butenyl, 3-methylbut-2-enyl, n-pentenyl, heptenyl, octenyl, decenyl, and the like. Reference to "alkyl" or "alkyl group" includes unsubstituted and substituted forms of the hydrocarbon group.

As used herein, "alkyne" refers to straight or branched chain hydrocarbon groups having 2 to 40, 2 to 20, 2 to 10, or 2 to 5 carbon atoms and at least one triple carbon to carbon bond. Reference to "alkyne" includes unsubstituted and substituted forms of the hydrocarbon.

As used herein, "alkynyl" or "alkynyl group" refers to straight or branched chain hydrocarbon groups having 2 to 40, 2 to 20, 2 to 10, or 2 to 5 carbon atoms and at least one triple carbon to carbon bond, such as ethynyl. Reference to "alkynyl" or "alkynyl group" includes unsubstituted and substituted forms of the hydrocarbon group.

As used herein, "aromatic" refers to a monocyclic or multicyclic ring system of 6 to 20 or 6 to 10 carbon atoms having alternating double and single bonds between carbon atoms. Exemplary aromatic groups include benzene, naphthalene, and the like. Reference to "aromatic" includes unsubstituted and substituted forms of the hydrocarbon.

As used herein the term "aryl" refers to an optionally substituted mono- or bicyclic carbocyclic ring system having one or two aromatic rings including, but not limited to, phenyl, benzyl, naphthyl, tetrahydronaphthyl, indanyl, indenyl, and the like. AOptionally substituted aryl@ includes aryl compounds having from zero to four substituents, and Asubstituted aryl@ includes aryl compounds having one or more substituents. The term ($C_5$-$C_8$ alkyl)aryl refers to any aryl group which is attached to the parent moiety via the alkyl group.

The term "bicyclic" represents either an unsaturated or saturated stable 7- to 12-membered bridged or fused bicyclic carbon ring. The bicyclic ring may be attached at any carbon atom which affords a stable structure. The term includes, but is not limited to, naphthyl, dicyclohexyl, dicyclohexenyl, and the like.

By "chemically feasible" is meant a bonding arrangement or a compound where the generally understood rules of organic structure are not violated. The structures disclosed herein, in all of their embodiments are intended to include only "chemically feasible" structures, and any recited structures that are not chemically feasible, for example in a structure shown with variable atoms or groups, are not intended to be disclosed or claimed herein.

As used herein, "cyclic" hydrocarbon refers to any stable 4, 5, 6, 7, 8, 9, 10, 11, or 12 membered, (unless the number of members is otherwise recited), monocyclic, bicyclic, or tricyclic cyclic ring.

As used herein, a "derivative" of a compound refers to a chemical compound that may be produced from another compound of similar structure in one or more steps, as in replacement of H by an alkyl, acyl, or amino group.

As used herein, "halo", "halogen", "halide", or "halogen radical" refers to a fluorine, chlorine, bromine, iodine, and astatine, and radicals thereof. Further, when used in compound words, such as "haloalkyl" or "haloalkenyl", "halo" refers to an alkyl or alkenyl radical in which one or more hydrogens are substituted by halogen radicals. Examples of haloalkyl include, but are not limited to, trifluoromethyl, trichloromethyl, pentafluoroethyl, and pentachloroethyl.

The term "haloalkyl" as used herein refers to an alkyl radical bearing at least one halogen substituent, for example, chloromethyl, fluoroethyl or trifluoromethyl and the like.

"Heteroaryl" refers to any stable 5, 6, 7, 8, 9, 10, 11, or 12 membered, (unless the number of members is otherwise recited), monocyclic, bicyclic, or tricyclic heterocyclic ring that is aromatic, and which consists of carbon atoms and 1, 2, 3, or 4 heteroatoms independently selected from the group consisting of N, O, and S. If the heteroaryl is defined by the number of carbons atoms, then 1, 2, 3, or 4 of the listed carbon atoms are replaced by a heteroatom. If the heteroaryl group is bicyclic or tricyclic, then at least one of the two or three rings must contain a heteroatom, though both or all three may each contain one or more heteroatoms. If the heteroaryl group is bicyclic or tricyclic, then only one of the rings must be aromatic. The N group may be N, NH, or N-substituent, depending on the chosen ring and if substituents are recited. The nitrogen and sulfur heteroatoms may optionally be oxidized (e.g., S, S(O), S(O)$_2$, and N—O). The heteroaryl ring may be attached to its pendant group at any heteroatom or carbon atom that results in a stable structure. The heteroaryl rings described herein may be substituted on carbon or on a nitrogen atom if the resulting compound is stable."

The term "heteroatom" means for example oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring.

"Heterocycle" refers to any stable 4, 5, 6, 7, 8, 9, 10, 11, or 12 membered, (unless the number of members is otherwise recited), monocyclic, bicyclic, or tricyclic heterocyclic ring that is saturated or partially unsaturated, and which consists of carbon atoms and 1, 2, 3, or 4 heteroatoms independently selected from the group consisting of N, O, and S. If the heterocycle is defined by the number of carbons atoms, then from 1, 2, 3, or 4 of the listed carbon atoms are replaced by a heteroatom. If the heterocycle is bicyclic or tricyclic, then at least one of the two or three rings must contain a heteroatom, though both or all three may each contain one or more heteroatoms. The N group may be N, NH, or N-substituent, depending on the chosen ring and if substituents are recited. The nitrogen and sulfur heteroatoms optionally may be oxidized (e.g., S, S(O), S(O)$_2$, and N—O). The heterocycle may be attached to its pendant group at any heteroatom or carbon atom that results in a stable structure. The heterocycles described herein may be substituted on carbon or on a nitrogen atom if the resulting compound is stable.

The term "$C_1$-$C_n$ alkyl" wherein n is an integer, as used herein, represents a branched or linear alkyl group having from one to the specified number of carbon atoms. Typically, $C_1$-$C_6$ alkyl groups include, but are not limited to, methyl, ethyl, n-propyl, iso-propyl, butyl, iso-butyl, sec-butyl, tert-butyl, pentyl, hexyl, and the like.

The term "$C_2$-$C_n$ alkenyl" wherein n is an integer, as used herein, represents an olefinically unsaturated branched or linear group having from 2 to the specified number of carbon atoms and at least one double bond. Examples of such groups include, but are not limited to, 1-propenyl, 2-propenyl, 1,3-butadienyl, 1-butenyl, hexenyl, pentenyl, and the like.

The term "$C_2$-$C_n$ alkynyl" wherein n is an integer refers to an unsaturated branched or linear group having from 2 to the specified number of carbon atoms and at least one triple bond. Examples of such groups include, but are not limited to, 1-propynyl, 2-propynyl, 1-butynyl, 2-butynyl, 1-pentynyl, and the like.

The term "$C_3$-$C_n$ cycloalkyl" wherein n=8, represents cyclopropyl, cyclobutyl, cyclopentyl, cyclohexyl, cycloheptyl, and cyclooctyl.

As used herein, the term "optionally substituted" typically refers to from zero to four substituents, wherein the substituents are each independently selected. Each of the independently selected substituents may be the same or different than other substituents. For example, the substituents of an R group of a formula may be optionally substituted (e.g., from 1 to 4 times) with independently selected H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain and amino acid.

The term "substituted" refers to any one or more hydrogen atoms on the designated atom (e.g., a carbon atom) that can be replaced with a selection from the indicated group (e.g., halide, hydroxyl, alkyl, and the like), provided that the designated atom's normal valence is not exceeded.

The compounds of the present disclosure contain one or more asymmetric centers in the molecule. In accordance with the present disclosure a structure that does not designate the stereochemistry is to be understood as embracing all the various optical isomers, as well as racemic mixtures thereof.

The compounds of the present disclosure may exist in tautomeric forms and an aspect of the present disclosure can include both mixtures and separate individual tautomers. For example the following structure:

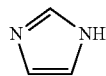

is understood to represent a mixture of the structures:

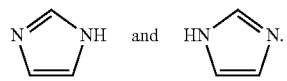

Discussion

Aspects of the present disclosure include compositions including an iminium catalyst, methods of making, methods of using, and the like. In addition, catalysis of aliphatic C—H hydroxylation by iminium catalyst is presented. The method allows for the selective organocatalytic hydroxylation of unactivated 3° C.—H bonds at room temperature using hydrogen peroxide as the terminal oxidant. Hydroxylation of an unactivated 2° C.—H bond is also demonstrated. Furthermore, improved functional group compatibility over other catalytic methods is reported in the form of selectivity for aliphatic C—H hydroxylation over alcohol oxidation. Based on initial mechanistic studies, an oxazirdinium species is proposed as the active oxidant.

Without wishing to be bound by any particular theory, it was hypothesized that these cationic oxidants, if properly developed, would potentially be more reactive than dioxiranes or oxaziridines in a C—H oxidation process due to increased electrophilicity of the oxygen atom.

In a particular aspect, a trifluoromethyl-substituted N-methyl iminium salt is capable of catalyzing the selective hydroxylation of aliphatic C—H bonds by hydrogen peroxide at room temperature, demonstrating improved reactivity over benxozathiazine catalysts. In addition, it is further disclosed that the catalyst is selective for tertiary aliphatic C—H hydroxylation over 1° and 2° alcohol oxidation, demonstrating a significant advantage over other hydroxylation methods in terms of functional group compatibility.

In an aspect, iminium catalysts as described here can be trifluoromethyl-substituted N-methyl iminium salts, for example. Iminium catalysts herein can catalyze the selective hydroxylation of aliphatic C—H bonds by hydrogen peroxide or other hydroxyl-donors at room temperature. Iminium catalysts as described herein can additionally be selective for tertiary aliphatic C—H hydroxylation over primary and secondary alcohol oxidation.

Iminium catalysts as described herein can be of the general formula:

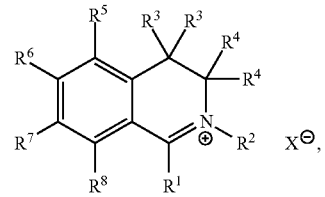

where:

$R^1$ can be —H, $C_6F_5$, —$CF_3$, —$CH_2CF_3$, —$CF_2CF_3$, —$CF_2CF_2CF_3$, $C_nF_{n+2}$, alkyl, aryl, fluorinated aryl, cycloalkyl, fluorinated cycloalkyl, or —$CO_2R$, $C(O)CO_2R$, where R can be any alkyl, alkenyl, alkynyl, or aryl group, or substituted versions thereof.

$R^2$ can be —$CH_3$, -Ph, —$C_6F_5$, —$CF_3$, —$CH_2Ph$, -cyclohexyl, -adamantyl, -cyclopropyl, —$C_nH_{n+2}$, $C_nF_{n+2}$, biphenyl, substituted biphenyl, alkyl, substituted alkyl, perfluoroalkyl, aryl, perfluroraryl, substituted aryl, or glycosyl.

$R^3$ can be —$CH_3$, —$CH_2CH_2$—, -Ph, —$CH_2Ph$, —OR, $COCH_3$, —$CO_2CH_3$, —$C_nH_{n+2}$, $C_n$, $F_{n+2}$, cycloalkyl, substituted cycloalkyl, aryl, or perfluoroaryl. In certain aspects, the two $R^3$ substituents can be $R^{3a}$ and $R^{3b}$, respectively, and $R^{3a}$ and $R^{3b}$ can be the same or can be different.

$R^4$ can be —$CH_3$, —$CH_2CH_2$—, —F, —$CF_3$, alkyl, substituted alkyl, perfluoroalkyl, cycloalkyl, substituted cycloalkyl, or perfluorocycloalkyl. In certain aspects, the two $R^4$ substituents can be $R^{4a}$ and $R^{4b}$, respectively, and $R^{4a}$ and $R^{4b}$ can be the same or can be different.

$R^5$ can be —H, —F, —Cl, —Br, —I, $CF_3$, —$C_6F_5$, —$NO_2$, —$OCH_3$, Ph, -p-$C_6H_4NO_2$, —OH, or alkyl.

$R^6$ can be —H, —F, —Cl, —Br, —I, $CF_3$, —$C_6F_5$, —$NO_2$, —$OCH_3$, Ph, -p-$C_6H_4NO_2$, —OH, or alkyl.

$R^7$ can be —H, —F, —Cl, —Br, —I, $CF_3$, —$C_6F_5$, —$NO_2$, —$OCH_3$, Ph, -p-$C_6H_4NO_2$, —OH, or alkyl.

$R^8$ can be —H, —F, —Cl, —Br, —I, $CF_3$, —$C_6F_5$, —$NO_2$, —$OCH_3$, Ph, -p-$C_6H_4NO_2$, $CH_2Ph$, -t-Bu, i-Pr, —OH, or alkyl.

Any one or more of $R^1$-$R^8$ can be optionally substituted or can be H, or independently optionally substituted or H. $R^1$-$R^8$ can be selected independently.

X can be —BF$_4^-$, —BPh$_4^-$, SbF$_6^-$, PF$_6^-$, ClO$_4^-$, —CF$_3$CO$_2^-$, CH$_3$SO$_3^-$, F$^-$, Cl$^-$, Br$^-$, I$^-$, tetrakis(3,5-bis(trifluoromethyl)phenyl)borate, —BR$_4$, or a pharmaceutically acceptable salt thereof.

In an aspect, the iminium catalyst does not have the following structure:

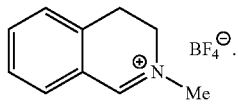

In an aspect, the iminium catalyst has the structure

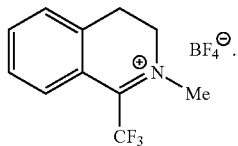

or a derivative thereof.

In an aspect, the iminium catalyst has the structure

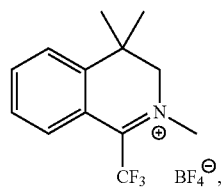

or a derivative thereof.

In an aspect, the iminium catalyst has the structure

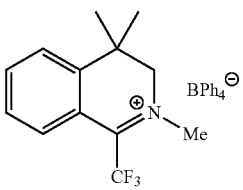

or a derivative thereof.

In other embodiments, an iminium catalyst can have the following formula:

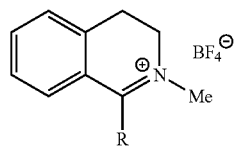

and R can be C$_6$F$_5$, CF$_3$, CH$_2$CF$_3$, —CF$_2$CF$_3$, CF$_2$CF$_2$CF$_3$, or C$_n$F$_{n+2}$.

Iminium catalyst of the present disclosure can be prepared using methods described in the Examples.

Iminium catalyst of the present disclosure can be used for aliphatic C—H hydroxylation. Iminium catalyst of the present disclosure can provide for the selective organocatalytic hydroxylation of unactivated 3° C.—H bonds and hydroxylation of an unactivated 2° C.—H bond is also demonstrated. Additional details are provided in the Examples.

As can be understood, the present application provides compositions and methods to synthesize highly active iminium salts with the catalytic activity disclosed herein. In one aspect, the iminium salts are highly reactive catalysts for aliphatic C—H hydroxylation. Possible advantages over other organocatalysts can include efficient hydroxylation at room temperature and hydroxylation of unactivated 2° C.—H bonds. Furthermore, chemoselectivity for aliphatic hydroxylation over alcohol oxidation provides advantages over existing catalysts, including the ability to oxidize a 2° aliphatic C—H bond selectively to a 20 alcohol with limited overoxidation. Overall, these results further establish organocatalysis as a competitive alternative to transition metal catalysis for aliphatic C—H hydroxylation.

EXAMPLES

We first investigated known epoxidation catalyst 3a[12d] at 20 mol % loading using an excess of hydrogen peroxide as the terminal oxidant but observed no hydroxylation of ester 1 at room temperature (Table 1, entry 1). Trifluoromethyl substitution as in catalyst 3b (entry 2) led to improved reactivity, generating the product of hydroxylation at the site remote to the benzoate ester. Incorporating gem-dimethyl substitution at the benzylic position to limit the possibility of catalyst aromatization[12d] led to a dramatic improvement (entry 3). Importantly, N-methyl substitution of the catalyst is required; neither the corresponding imine nor its HBF$_4$ salt are competent hydroxylation catalysts under these conditions (entries 4&5). The use of hexafluoroisopropanol (HFIP), known to activate H$_2$O$_2$,[13] as a solvent was essential; varying the amount used allowed for the identification of fully optimized conditions (entry 8).

TABLE 1

Summary of optimization studies.[a]

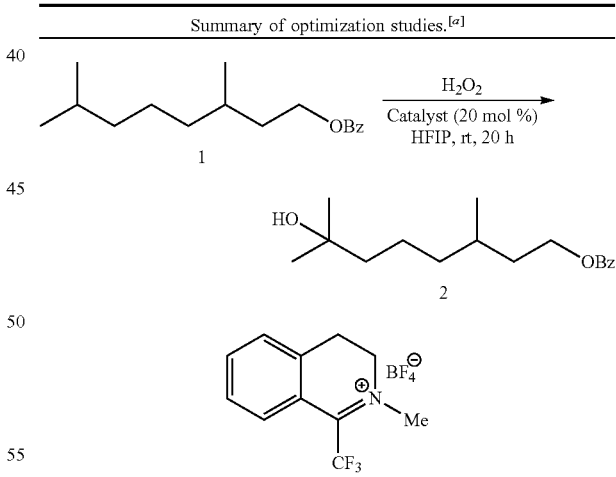

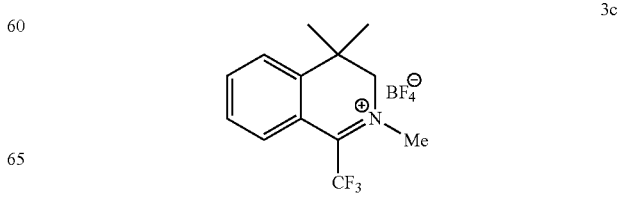

TABLE 1-continued

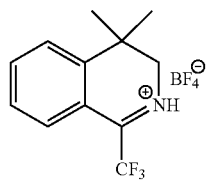

3d

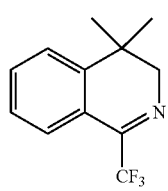

3e

| Entry | Catalyst | Deviation from initially optimized conditions[b] | Conversion (%)[c] | Yield of 2 (%)[d] |
|---|---|---|---|---|
| 1 | 3a | — | <1 | <1 |
| 2 | 3b | — | 12 | 3 |
| 3 | 3c | — | 70 | 57 |
| 4 | 3d | — | <1 | <1 |
| 5 | 3e | — | <1 | <1 |
| 6 | 3c | DCE (200 µL) | 31 | 21 |
| 7 | 3c | MeCN (200 µL) | 2 | <1 |
| 8 | 3c | 200 µL HFIP | 74 | 64 |

[a]Reactions performed with 0.2 mmol substrate, 0.04 mmol 3c, and 180 µL $H_2O_2$ (50% aqueous, 16 equiv) in 150 µL HFIP at room temperature for 20 h, unless otherwise noted.
[b]Entries 6&7: DCE and MeCN were used as co-solvents in addition to HFIP. Entry 8: The amount of HFIP was varied.
[c]Determined by GC.
[d]Corrected GC yield.

Note that the R group of the generic formula of Table 1 that encompasses 3a and 3b also includes the additional R substituents as provided for the generic formula later in this section, wherein the formula has 8 R groups.

Figure 2:
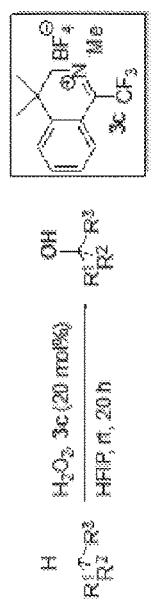
FIG. 2 illustrate the hydroxylation of C—H bonds by catalysts described herein. Reactions performed on 0.4 mmol scale. Yields of isolated products and, in parentheses, combined yield of product and recovered starting material following chromatography. [b] Determined by GC of crude reaction mixture using authentic standards. [c]40 mol % of 3c was used. [d] Reaction time=48 h. 3c and $H_2O_2$ added in two portions at 0 and 24 h.

Notably, iminium salt 3b demonstrated improved reactivity over other organocatalysts, which require elevated temperatures and in some cases extended reaction times to achieve similar results. Thus, we investigated a variety of substrates to evaluate functional group compatibility and electronic effects on yield and selectivity (FIG. 2). As is the case for other catalysts, hydroxylation using 3c is consistently selective for 3° over 2° oxidation. Additionally, we typically observed selectivity for a single site of hydroxylation. Furthermore, this catalyst demonstrates a high degree of selectivity for hydroxylation of 3° C.—H bonds that are remote rather than proximal to an electron-withdrawing group. For example, we directly compared the selectivity of hydroxylation of 3,7-dimethyloctyl acetate (generating 4 as the major product) using 3c to the selectivity obtained using the White-Chen catalyst. In the latter case the reported selectivity for hydroxylation of the remote over the proximal 3° C.—H bond is 5:1.[5b] In contrast, with catalyst 3c we observed 19:1 selectivity. Hydroxylation catalyzed by 3c is also stereospecific (product 9).

Figure 3:
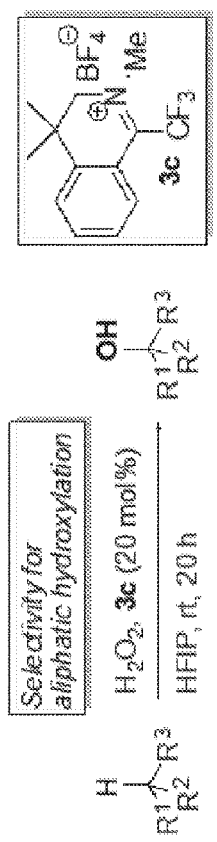
FIG. 3 illustrates aliphatic hydroxylation of alcohol and ether substrates. Reactions performed on 0.4 mmol scale. Yields of isolated products and, in parentheses, combined yield of product and recovered starting material following chromatography. [b] Recovery of starting material is low due to difficult re-isolation. Ratios determined by GC. Corrected GC yield. Reaction was performed with the addition of 400 µL of $CH_2Cl_2$. $CH_2Cl_2$ (200 µL) was used as a cosolvent.
Figure 3:
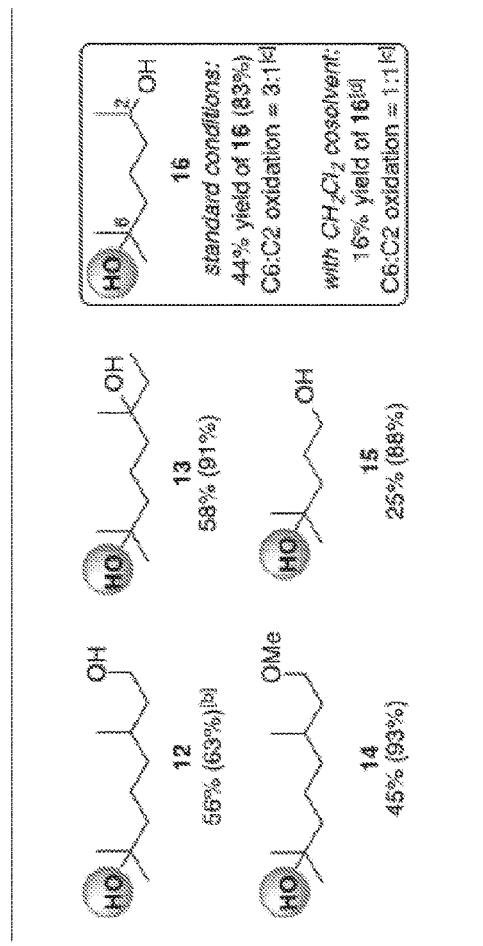
Figure 3:
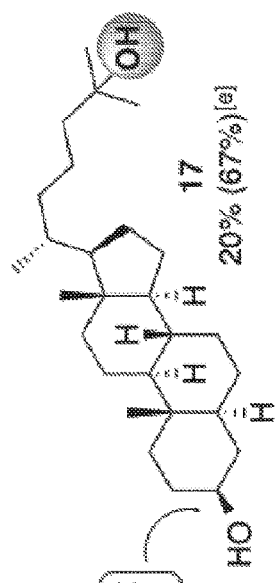

We also observed an unexpected preference for aliphatic hydroxylation in the presence of sterically unencumbered 1° and 2° alcohols (FIG. 3). To our knowledge this type of chemoselectivity is unprecedented for organocatalysts or transition metal catalysts that exhibit site-selectivity; the use of ester protecting groups is generally required to avoid alcohol oxidation.[4-9] In our case, the oxidation of 1° alcohols (e.g. products 12 and 15) using 3c generates no more than trace amounts of carboxylic acid or aldehyde products.[14]

Aliphatic hydroxylation also occurs selectively over oxidation of 2° alcohols (e.g. product 16), although the degree of selectivity (3:1 preference) is diminished. These counterintuitive results can potentially be explained by unexpected hydrophobic effects elucidated by Breslow for iminium salt-catalyzed epoxidations.[15] To test this hypothesis, we performed a hydroxylation of 6-methylheptan-2-ol using our standard conditions but with the inclusion of dichloromethane as a cosolvent (FIG. 3, 1:1 ratio with HFIP).

Consistent with our hypothesis, there was no selectivity for aliphatic hydroxylation in this less polar solvent system; a 1:1 mixture of 16 and 6-methylheptane-2-one was observed. Addition of a smaller amount of $CH_2Cl_2$ (1:2 ratio with HFIP) to solubilize dihydrocholesterol was sufficient to maintain selectivity for aliphatic hydroxylation (product 17). Notably, in this case no 2° alcohol oxidation was observed.

Hydroxylation of unactivated 2° aliphatic C—H bonds has been reported using transition metal catalysts but not organocatalysts, a drawback we surmised might be overcome by the improved reactivity of 3c. Furthermore, one current limitation of aliphatic 2° bond hydroxylation by site-selective catalysts is that ketones are typically observed as the only product.[4] In contrast, 3c is not only capable of catalyzing the oxidation of cyclohexane, but the typically observed overoxidation to the ketone is suppressed (Scheme 1).[16] In this case the addition of $CH_2Cl_2$ modestly improved the yield due to increased solubility of the substrate in the biphasic solvent mixture (product ratio did not change).

Scheme 1. Selective catalytic oxidation of cyclohexane to cyclohexanol using 3C

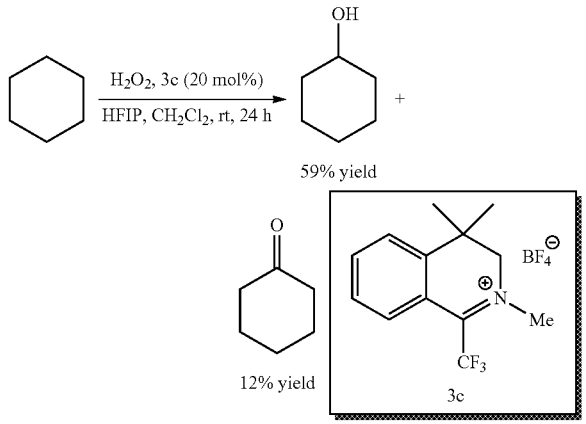

Figure 4A:
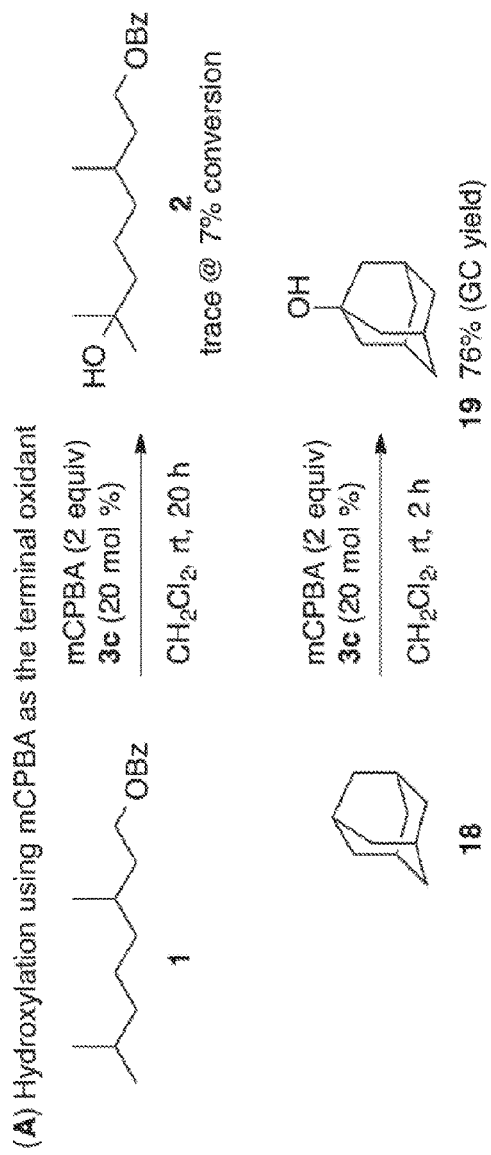
FIG. 4A illustrates an aspect of investigation of the reaction mechanism and hydroxylation using mCPBA as the terminal oxidant.
Figure 4B:
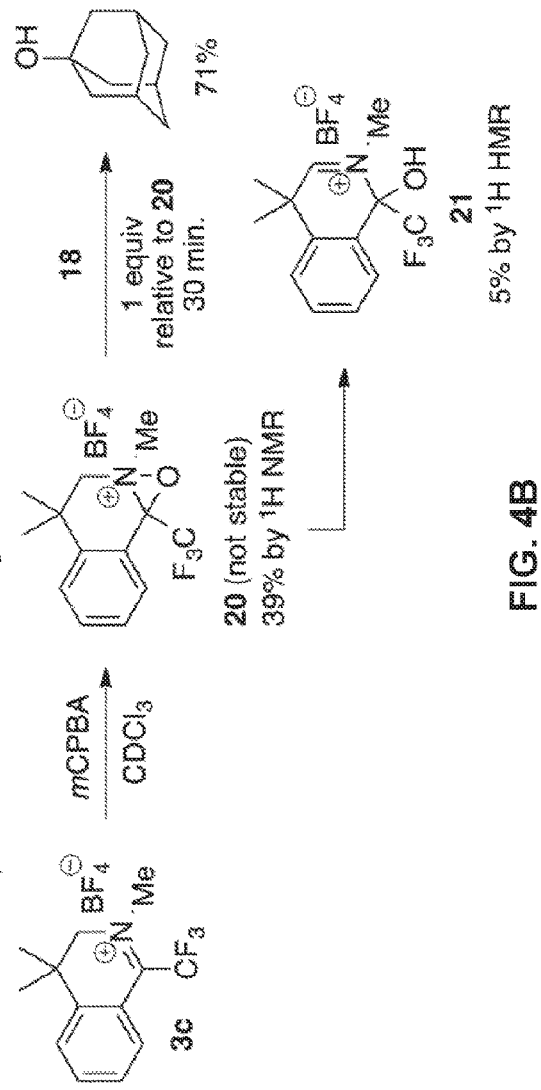
FIG. 4B illustrates an aspect of investigation of the reaction mechanism and observation of putatitive oxaziridinium by $^1$H NMR.
Figure 4C:
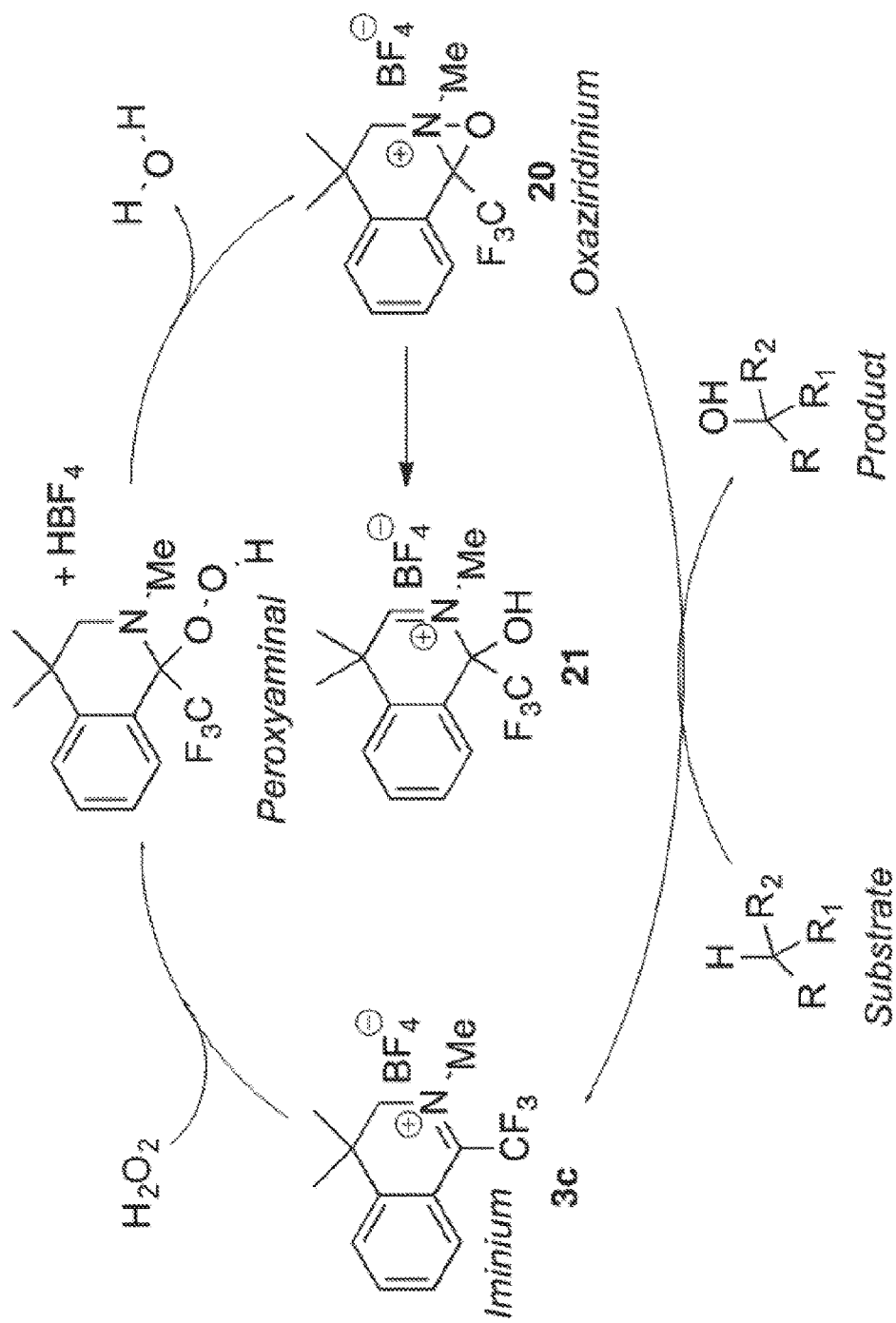
FIG. 4C illustrates an aspect of investigation of the reaction mechanism and a proposed catalytic cycle.

Initial attempts to observe the formation of an oxaziridinium species under the standard reaction conditions were unsuccessful. Thus to investigate the mechanism further we performed catalytic oxidations using mCPBA, the oxidant of choice for oxaziridinium synthesis,[10] as the terminal oxidant (FIG. 4A). In this case, hydroxylation of 1 to form 2 was low-yielding, but adamantane was smoothly converted to 1-adamantanol in just 2 h. The formation of a species consistent with an oxaziridinium could be observed by $^1H$ NMR, but could not be isolated due to considerable instability (FIG. 4B). Iminium 21, the result of a known decomposition pathway of oxaziridinium species, was also observed and could be isolated. In the same experiment, addition of adamantane to the NMR tube let to the consumption of 20 and concomitant formation of 1-adamantanol. Thus, the evidence suggests that an oxaziridinium species is capable of hydroxylation at room temperature and is therefore the likely active oxidant. In support of this, the formation of 21 is also observed under the optimized reaction conditions. A proposed catalytic cycle is outlined in FIG. 4C. We propose that $HBF_4$ liberated upon addition of hydrogen peroxide promotes oxaziridinium formation, which is consistent with a pH of 2 observed for the standard reaction conditions. Iminium 21 can catalyze the hydroxylation of 1 under the standard reaction conditions but in a much lower yield (5%), suggesting an explanation for the limitations in reaction conversion.

Synthesis and Compounds

Catalyst

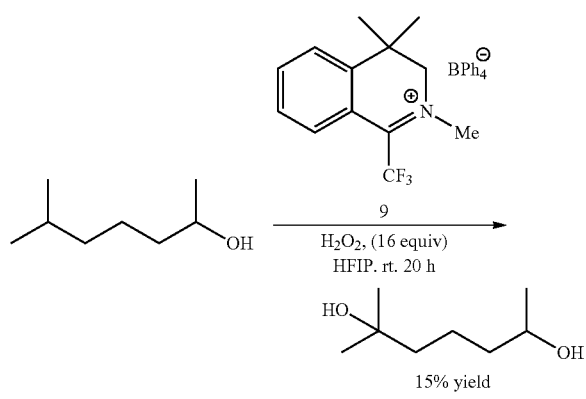

The present application provides compositions and methods to synthesize highly active iminium salts with the catalytic activity disclosed herein. In one aspect, the iminium salts include trifluoromethyl iminium salts. The iminium salts are highly reactive catalysts for aliphatic C—H hydroxylation.

In conclusion, we have developed a trifluoromethyl iminium salt as a highly reactive catalyst for aliphatic C—H hydroxylation. Advantages over other organocatalysts include efficient hydroxylation at room temperature and hydroxylation of unactivated 2° C.—H bonds. Furthermore, chemoselectivity for aliphatic hydroxylation over alcohol oxidation provides advantages over existing catalysts, including the ability to oxidize a 2° aliphatic C—H bond selectively to a 20 alcohol with limited overoxidation. Overall, these results further establish organocatalysis as a competitive alternative to transition metal catalysis for aliphatic C—H hydroxylation.

BIBLIOGRAPHY

[1] For reviews and perspectives, see: a) T. Newhouse, P. S. Baran, *Angew. Chem. Int. Ed.* 2011, 50, 3362-3374; *Angew. Chem.* 2011, 123, 3422-3434. b) M. C. White, *Science* 2012, 335, 807-809.

[2] J. M. Howell, K. Feng, J. R. Clark, L. J. Trzepkowski, M. C. White, *J. Am. Chem. Soc.* 2015, 137, 14590-14593.

[3] P. E. Gormisky, M. C. White, *J. Am. Chem. Soc.* 2013, 135, 14052-14055.

[4] a) S. Lee, P. L. Fuchs, *J. Am. Chem. Soc.* 2002, 124, 13978-13979. b) M. S. Chen, M. C. White, *Science* 2007, 318, 783-787. c) M. S. Chen, M. C. White, *Science* 2010, 327, 566-571. d) E. McNeill, J. Du Bois, *J. Am. Chem. Soc.* 2010, 132, 10202-10204. e) M. Zhou, N. D. Schley, R. H. Crabtree, *J. Am. Chem. Soc.* 2010, 132, 12550-12551. f) E. McNeill, J. Du Bois, *Chem. Sci.* 2012, 3, 1810-1813.

[5] D. W. C. MacMillan, *Nature* 2008, 455, 304-308.

[6] a) B. H. Brodsy, J. Du Bois, *J. Am. Chem. Soc.* 2005, 127, 15291-15393. b) N. D. Litvinas, B. H. Brodsky, J. Du Bois, *Angew. Chem. Int. Ed.* 2009, 48, 4513-4516; *Angew. Chem.* 2009, 121, 4583-4586. c) A. M. Adams, J. Du Bois, *Chem. Sci.* 2013, 5, 656.

[7] C. J. Pierce, M. K. Hilinski, *Org. Lett.* 2014, 16, 6504-6507.

[8] a) R. Curci, A. Dinoi, M. F. Rubino, *Pure and Applied Chemistry* 1995, 67, 811-822. b) R. Curci, L. D'Accolti, C. Fusco, *Acc. Chem. Res.* 2006, 39, 1-9. c) C. Annese, L. D'Accolti, C. Fusco, R. Curci, *Org. Lett.* 2011, 13, 2142-2144.

[9] a) D. D. DesMarteau, A. Donadelli, V. Montanari, V. A. Petrov, G. Resnati, *J. Am. Chem. Soc.* 1993, 115, 4897-4898. b) A. Arnone, M. Cavicchioli, V. Montanari, G. Resnati, *J. Org. Chem.* 1993, 59, 5511-5513. c) V. A. Petrov, G. Resnati, *Chem. Rev.* 1996, 96, 1809-1823.

[10] a) P. Milliet, A. Picot, X. Lusinchi, *Tetrahedron Lett.* 1976, 17, 1573-1576. b) G. Hanquet, X. Lusinchi, P. Milliet, *Tetrahedron Lett.* 1987, 28, 6061-6064.

[11] a) L. Bohé, G. Hanquet, M. Lusinchi, X. Lusinchi, *Tetrahedron Lett.* 1993, 34, 7271-7274. b) X. Lusinchi, G. Hanquet, *Tetrahedron* 1997, 53, 13727-13738. c) L. Bohé, M. Lusinchi, X. Lusinchi, *Tetrahedron* 1999, 55, 141-154. d) R. E. del Rio, B. Wang, A. S Achab, L. Bohé, *Org. Lett.* 2007, 9, 2265-2268.

[12] a) P. C. B. Page, G. A. Rassias, D. Barros, D. Bethell, M. B. Schilling, *J. Chem. Soc., Perkin Trans.* 1 2000, 3325-3334. b) P. C. B. Page, G. A. Rassias, D. Barros, A. Ardakani, B. Buckley, D. Bethell, T. A. D. Smith, A. M. Z. Slawin, *J. Org. Chem.* 2001, 66, 6926-6931. c) L. Bohé, M. Kammoun, *Tetrahedron Letters* 2002, 43, 803-805. d) L. Bohé, M. Kammoun, *Tetrahedron Letters* 2004, 45, 747-751. e) P. C. B. Page, M. M. Farah, B. R. Buckley, A. J. Blacker, *J. Org. Chem.* 2007, 72, 4424-4430. f) R. Novikov, G. Bernardinelli, J. Lacour, *Adv. Synth. Catal.* 2009, 351, 596-606. g) R. Novikov, J. Lacour, *Tetrahedron: Asymmetry* 2010, 21, 1611-1618. h) P. C. B. Page, L. F. Appleby, Y. Chan, D. P. Day, B. R. Buckley, A. M. Z. Slawin, S. M. Allin, M. J. McKenzie, *J. Org. Chem.* 2013, 78, 8074-8082. i) B. Buckley, C. Elliott, Y. Chan, N. Dreyfus, P. C. B. Page, *Synlett* 2013, 24, 2266-2270. j) P. C. B. Page, Y. Chan, J. Liddle, M. R. J. Elsegood, *Tetrahedron* 2014, 70, 7283-7305.

[13] K. Neimann, R. Neumann, *Org. Lett.* 2000, 2, 2861-2863.

[14] In contrast, alcohol oxidation dominated the product distribution during attempted hydroxylation of alcohol substrates using the White-Chen catalyst (see Supporting Information). Benzoxathiazine catalysts have been reported to readily oxidize alcohols (see ref 6a).

[15] M. R. Biscoe, R. Breslow, *J. Am. Chem. Soc.* 2005, 127, 10812-10813.

[16] Determined by GC. See Supporting Information for details.

Supporting Information

I. General Information

All reagents were obtained commercially in reagent grade or better quality and used without further purification. Anhydrous solvents were obtained from a Pure Process Technology solvent purification system. Flash column chromatography was performed using silica gel (230-400 mesh) purchased from Fisher Scientific. $^1H$, $^{13}C$, and $^{19}F$ NMR spectra were measured on a Varian Inova 600 (600 MHz) spectrometer and acquired at 300 K. Chemical shifts are reported in parts per million (ppm δ) referenced to the residual $^1$H or $^{13}$C resonance of the solvent. Trifluoroacetic acid was used as an external reference for $^{19}$F NMR. The following abbreviations are used singularly or in combination to indicate the multiplicity of signals: s—singlet, d—doublet, t—triplet, q—quartet, m—multiplet and br—broad. Gas chromatography was performed using an Agilent 7820A GC equipped with an autosampler and FID detector. Dodecane was used as an internal standard for GC yield calculations, which are corrected based on experimentally determined burn ratios of the compounds of interest to dodecane. IR spectra were recorded on a Shimadzu IRAffinity-1S. Mass spectrometry data using ESI or APCI ionization mode to minimize fragmentation were collected on an Agilent 6120 Single Quadrupole LC/MS instrument equipped with an ESI/APCI multimode source. HRMS data were obtained from the School of Chemical Sciences Mass Spectrometry Laboratory at the University of Illinois at Urbana-Champaign and are accurate to within 5 ppm.

II. Synthesis of Iminium Catalysts 3,4-Dihydro-2-methylisoquinolinium tetrafluoroborate (3a)

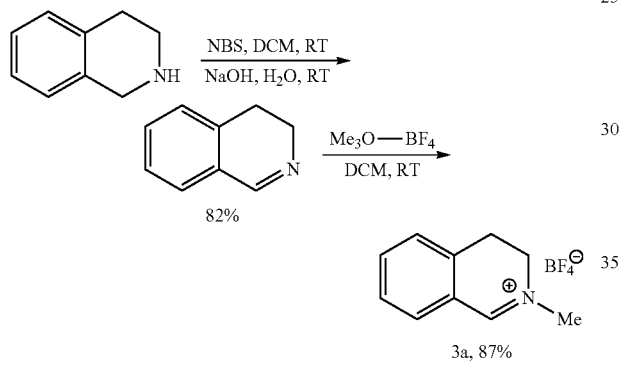

Compound 3a was prepared according to the reported procedure [1,2]. $^1$H NMR (600 MHz, Acetone-d$_6$): δ 9.21 (s, 1H), 7.90 (d, J=7.6 Hz, 1H), 7.82 (td, J=7.6, 1.3 Hz, 1H), 7.56 (t, J=7.6 Hz, 1H), 7.54 (d, J=7.6 Hz, 1H), 4.26 (t, J=8.1 Hz, 2H), 3.95 (s, 3H), 3.40 (t, J=8.1 Hz, 2H) ppm; $^{13}$C NMR (150 MHz Acetone-d$_6$): δ 167.00, 137.68, 136.44, 133.45, 128.33, 128.23, 124.94, 50.02, 47.38, 24.68 ppm.

3,4-Dihydro-2-methyl-1-(trifluoromethyl)isoquinolinium tetrafluoroborate (3b)

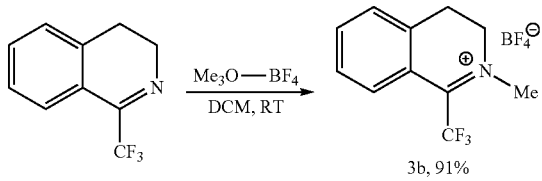

3,4-Dihydro-1-(trifluoromethyl)isoquinoline was prepared by following the reported procedure[3,4]. In a nitrogen glovebox, to a solution of 3,4-dihydro-1-(trifluoromethyl)isoquinoline (219 mg, 1.1 mmol) in anhydrous dichloromethane (2 mL) was added trimethyloxonium tetrafluoroborate (148 mg, 1.0 mmol). The mixture was stirred at room temperature for 15 hours, then removed from the glovebox. The solvent was removed under vacuum, and ethyl acetate (2 mL) was added. The resulting solid was filtered and dried to give pure 3b (276 mg, 0.92 mmol, 91%). $^1$H NMR (600 MHz, Acetone-d$_6$): δ 8.02 (d, J=8.0 Hz, 1H), 7.79 (td, J=7.6, 1.3 Hz, 1H), 7.68 (dd, J=7.7, 1.2 Hz, 1H), 7.61 (td, J=7.7, 1.2 Hz, 1H), 3.61 (m, 2H), 3.44 (t, J=8.1 Hz, 2H), 3.06 (t, J=5.6 Hz, 3H) ppm; $^{13}$C NMR (150 MHz Acetone-d$_6$): δ 140.1, 135.2, 133.1, 130.8 (q, J=4 Hz), 129.3, 127.9, 116.5 (q, J=292 Hz), 50.3 (t, J=16 Hz), 33.7 (t, J=16 Hz), 30.6 (t, J=5 Hz); $^{19}$F NMR (564 MHz Acetone-d$_6$): δ −71.69, −151.28 ppm; IR (film, cm$^{-1}$): 1700, 1602, 1573, 1464, 1294, 1143, 1016 (br), 938, 758, 741, 662; HRMS m/z (ESI$^+$): Calculated for $C_{11}H_{11}F_3N$ [M-BF$_4$]$^+$: 214.0838, found 214.0838.

3,4-Dihydro-2,4,4-trimethyl-1-(trifluoromethyl)isoquinolinium tetrafluoroborate (3c)

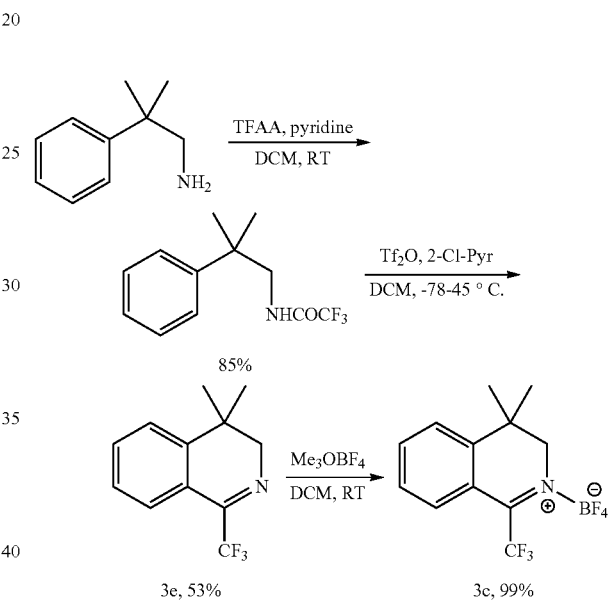

Under N$_2$ atmosphere, 2-methyl-2-phenyl-propan-1-amine [5] (7.4 g, 50 mmol) was mixed with anhydrous dichloromethane (65 mL) in a 250 mL flask with stirring bar. Pyridine (7.1 g, 90 mmol) was added to the stirring solution via syringe before trifluoroacetic anhydride (12.6 g, 60 mmol) was added dropwise. The reaction mixture was stirred at room temperature overnight. The light brown solution was washed with brine, dried over Na$_2$SO$_4$, and concentrated under vacuum. The residue was purified by flash chromatography (silica gel, hexanes/ether 4/1) to give 2,2,2-trifluoro-N-(2-methyl-2-phenylpropyl)acetamide (10.4 g, 42.4 mmol, 85%). $^1$H NMR (600 MHz, CDCl$_3$): δ 7.33-7.38 (4H, m), 7.26 (t, J=7.1 Hz, 1H), 5.89 (1H, br), 3.53 (d, J=6.2 Hz, 2H), 1.37 (6H, s) ppm; $^{13}$C NMR (150 MHz CDCl$_3$): δ 157.2 (q, J=36 Hz), 145.0, 128.9, 126.8, 125.7, 115.8 (q, J=286 Hz), 50.9, 38.7, 26.3 ppm; $^{19}$F NMR (564 MHz CDCl$_3$): δ −76.92 ppm; IR (film, cm$^{-1}$): 3320, 2972, 1706, 1552, 1152, 764, 698; HRMS m/z (ESI$^+$): Calculated for $C_{12}H_{14}F_3NO$ [M+H]$^+$: 246.1106, found 246.1105.

Under N$_2$ atmosphere, 2,2,2-trifluoro-N-(2-methyl-2-phenylpropyl)acetamide (3.8 g, 15.5 mmol), 2-chloropyridine (2.1 g, 18.6 mmol), and anhydrous dichloromethane (75 mL) were mixed in a 250 mL two-neck flask equipped with condenser and stirring bar. The solution was cooled to −78°

C. using a dry ice/acetone bath and then trifluoromethanesulfonic anhydride (4.8 g, 17.1 mmol) was added dropwise. After 5 min, the mixture was warmed to 0° C. in an ice/water bath. After stirring at 0° C. for one hour, the mixture was warmed to 45° C. and the stirring was continued for two days. The reaction mixture was cooled to room temperature before triethylamine (4.8 mL) was introduced carefully. The dark red solution was washed with brine, dried over $Na_2SO_4$, and concentrated under vacuum to obtain crude product, which was purified by flash chromatography (silica gel, hexanes/ether 25/1) to give 3,4-dihydro-4,4-dimethyl-1-(trifluoromethyl)-isoquinoline (3e) as pale yellow oil (1.86 g, 8.1 mmol, 53%). $^1$H NMR (600 MHz, CDCl$_3$): δ 7.61 (dt, J=7.9, 1.8 Hz, 1H), 7.50 (dt, J=7.7, 1.3 Hz, 1H), 7.41 (dd, J=7.9, 1.3 Hz, 1H), 7.32 (dt, J=7.7 Hz, 1H), 3.74 (q, J=1.9 Hz, 2H), 1.24 (s, 6H) ppm; $^{13}$C NMR (150 MHz CDCl$_3$): δ 155.5 (q, J=33 Hz), 146.7, 132.7, 126.7, 125.7 (q, J=3 Hz), 124.0, 121.9, 120.2 (q, J=276 Hz), 59.9, 31.7, 26.0 ppm; $^{19}$F NMR (564 MHz CDCl$_3$): δ −68.60 ppm; IR (film, cm$^{-1}$): 2965, 1646, 1450, 1363, 1185, 1120, 992, 945, 757, 734, 692, 583, 535; HRMS m/z (ESI$^+$): Calculated for $C_{12}H_{13}F_3N$ [M+H]$^+$: 228.1000, found 228.1003.

In a nitrogen glovebox, to a solution of 3,4-dihydro-4,4-dimethyl-1-(trifluoromethyl)-isoquinoline (499 mg, 2.2 mmol) in anhydrous dichloromethane (4 mL) was added trimethyloxonium tetrafluoroborate (296 rag, 2.0 mmol). The mixture was stirred at room temperature for 15 hours, then removed from the glovebox. The solvent was removed under vacuum and the resulting solid was washed with anhydrous diethyl ether (5 mL) and dried under high vacuum to give pure product (3c) as white solid (653 mg, 1.98 mmol, 99%). $^1$H NMR (600 MHz, Acetone-d$_6$): δ 8.10 (dd, J=7.9, 2.3 Hz, 1H), 8.05 (t, J=7.7 Hz, 1H), 7.84 (d, J=7.9 Hz, 1H), 7.70 (dt, J=7.7, 1.2 Hz, 1H), 4.45 (s, 2H), 4.30 (q, J=2.8 Hz, 3H), 1.49 (s, 6H) ppm; $^{13}$C NMR (150 MHz Acetone-d$_6$): δ 148.0, 139.7, 131.2 (q, J=5 Hz), 128.3, 125.2, 121.4, 118.4 (q, J=282 Hz), 65.8, 48.9 (q, J=5 Hz), 33.0, 24.1 ppm; $^{19}$F NMR (564 MHz Acetone-d$_6$): δ −57.20, −151.25 ppm; IR (film, cm$^{-1}$): 2976, 1655, 1599, 1571, 1447, 1372, 1346, 1204, 1158, 1035 (br), 785, 758, 706; HRMS m/z (ESI$^+$): Calculated for $C_{13}H_{15}F_3N$ [M-BF$_4$]$^+$: 242.1151, found 242.1156.

3,4-Dihydro-4,4-trimethyl-1-(trifluoromethyl)isoquinolinium tetrafluoroborate (3d)

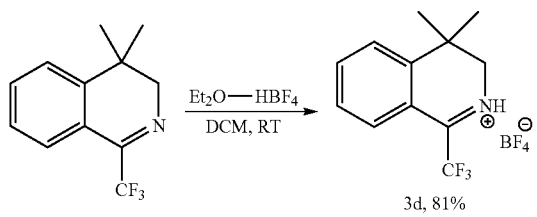

3d, 81%

Under N$_2$ atmosphere, to a solution of 3,4-dihydro-4,4-dimethyl-1-(trifluoromethyl)-isoquinoline (114 mg, 0.5 mmol) in anhydrous dichloromethane (1 mL) was added tetrafluoroboric acid diethyl ether complex (81 mg, 0.5 mmol). The mixture was stirred at room temperature for two hours. The solvent was removed under vacuum and the resulting solid was washed with anhydrous diethyl ether (1 mL) and dried under high vacuum to give pure product as white solid (128 mg, 0.41 mmol, 81%) $^1$H NMR (600 MHz, CDCl$_3$): δ 7.99 (d, J=8.0 Hz, 1H), 7.94 (td, J=7.7, 1.3 Hz, 1H), 7.64 (dd, J=8.0, 1.1 Hz, 1H), 7.59 (td, J=7.7, 1.1 Hz, 1H), 4.16 (d, J=1.2 Hz, 2H), 1.42 (s, 6H) ppm; $^{13}$C NMR (150 MHz CDCl$_3$): δ 149.4, 140.8, 131.8 (q, J=3.2 Hz), 1287, 125.6, 118.0, 117.5 (q, J=281 Hz), 53.8, 33.0, 25.8 ppm; $^{19}$F NMR (564 MHz CDCl$_3$): δ −66.05, −152.37 ppm; IR (film, cm$^{-1}$): 3087 (br), 1674, 1599, 1566, 1366, 1328, 1182, 1005 (br), 788, 758, 738, 583; HRMS m/z (ESI$^+$): Calculated for $C_{12}H_{13}F_3N$ [M-BF$_4$]$^+$: 228.1000, found 228.1011.

III. Preparation of Substrates 3,7-Dimethyl-1-octanol, 3,7-dimethyl-3-octanol, 6-methyl-2-heptanol, and (+)-dihydrocholesterol are commercially available, which were used as received for hydroxylation reaction. The following known compounds were synthesized by following the previously reported method: 3,7-dimethyloctyl benzoate [6], 3,7-dimethyloctyl acetate [6], 6-methylheptan-2-yl acetate [6], 2,2,2-trifluoro-N-(6-methylheptan-2-yl)acetamide [7], 4-methylpentyl benzoate [6], cis-4-methylcyclohexyl pivalate [6], 2-(3,7-dimethyloctyl) isoindoline-1,3-dione [8], methyl 3α-acetoxy-5β-cholan-24-oate [9], 1-methoxy-3,7-dimethyloctane [10].

4,8-dimethyl-1-(4-chlorophenyl)-1-nonanone

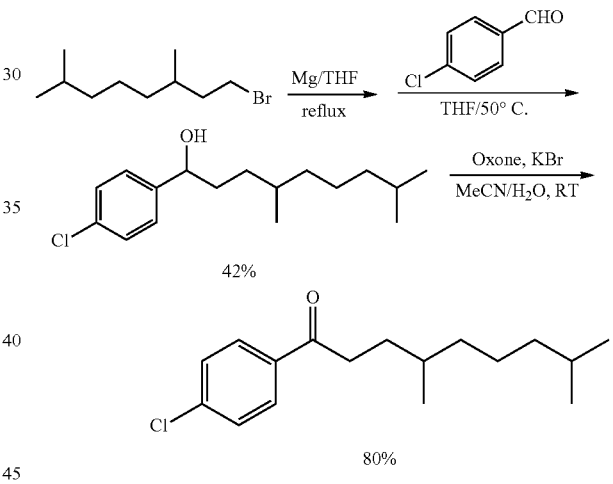

4,8-Dimethyl-1-(4-chlorophenyl)-1-nonanol was prepared according to reported procedure[11]. Under N$_2$ atmosphere, Mg (0.60 g, 25 mmol), a few iodine crystals, and dry THF (5 mL) were mixed in a two-neck flask equipped with condenser and stirring bar. A solution of 1-bromo-3,7-dimethyloctane (2.21 g, 10 mmol) in anhydrous THF (15 mL) was added slowly. The mixture was then refluxed for 4 hours. The resulting solution of Grignard reagent was then added to a solution of 4-chlorobenzaldehyde (1.40 g, 10 mmol) in anhydrous THF (10 mL) through a cannula. The mixture was heated to 50° C. and stirred overnight (18 h). After cooling to room temperature, the reaction was quenched with saturated aqueous NH$_4$Cl solution. The organic portion was extracted into dichloromethane, washed with brine, dried over MgSO$_4$, and concentrated under vacuum. The residue was purified by flash chromatography (silica gel, hexanes/EtOAc 30/1 to 10/1) to give pure product (1.20 g, 4.2 mmol, 42%). $^1$H NMR (600 MHz, CDCl$_3$): δ 7.30 (d, J=8.4 Hz, 2H), 7.26 (d, J=8.4 Hz, 2H), 4.61 (q, J=6.4, 5.9 Hz, 1H), 1.81-1.60 (m, 3H), 1.49 (septet, J=6.7 Hz, 1H), 1.43-1.35 (m, 1H), 1.27-1.15 (m, 4H), 1.12-1.00

(m, 3H), 0.82-0.85 (m, 9H) ppm; $^{13}$C NMR (151 MHz, CDCl$_3$) (two diastereomers) δ 143.4 (143.3), 133.1 (133.0), 128.5, 127.3 (127.2), 74.4 (74.3), 39.2, 37.1 (37.0), 36.7 (36.6), 32.84 (32.83), 32.68 (32.66), 27.9, 24.69 (24.67), 22.7, 22.6, 19.6 (19.5) ppm.

To a solution of 4,8-dimethyl-1-(4-chlorophenyl)-1-nonanol (1.13 g, 4.0 mmol) and KBr (47.6 mg, 0.4 mmol) in a mixture of MeCN (7.2 mL) and water (0.8 mL) was added Oxone (2.46 g, 4.0 mmol) at room temperature. The mixture was stirred overnight, quenched with saturated aqueous Na$_2$S$_2$O$_3$ (50 mL), and then extracted with EtOAc (3×50 mL). The combined organic solution was dried over MgSO$_4$ and concentrated under vacuum to give crude product, which was purified by flash chromatography (silica gel, hexanes/EtOAc 50/1) to obtain 4,8-dimethyl-1-(4-chlorophenyl)-1-nonanone as colorless oil (0.90 g, 3.2 mmol, 80%). $^1$H NMR (600 MHz, CDCl$_3$): δ 7.88 (d, J=8.6 Hz, 2H), 7.41 (d, J=8.6 Hz, 2H), 2.96-2.85 (m, 2H), 1.77-1.71 (m, 1H), 1.54-1.45 (m, 3H), 1.33-1.21 (m, 3H), 1.16-1.10 (m, 3H), 0.90 (d, J=6.4 Hz, 3H), 0.85 (d, J=6.6 Hz, 6H) ppm; $^{13}$C NMR (151 MHz, CDCl$_3$) δ 199.5, 139.2, 135.4, 129.5, 128.8, 39.2, 37.0, 36.3, 32.6, 31.3, 27.9, 24.7, 22.7, 22.6, 19.5 ppm; IR (film, cm$^{-1}$): 2954, 2926, 1685, 1589, 1462, 1205, 1092, 1013, 835, 734, 527; HRMS m/z (ESI$^+$): Calculated for C$_{17}$H$_{26}$ClO [M+H]$^+$: 281.1672, found 281.1659.

IV. Iminium-Catalyzed CH Hydroxylation

1. Optimization of Conditions for CH Hydroxylation Reaction 1.1 General Procedure for Catalyst Screen 3,7-Dimethyloctyl benzoate (52.4 mg, 0.2 mmol), catalyst (0.04 mmol), and hexafluoro-2-propanol (150 μL) were mixed in a 5 mL vial equipped with a stirring bar. H$_2$O$_2$ (181 μL, 50 wt. % in H$_2$O, 3.2 mmol) was then added in one portion. The reaction mixture was stirred at room temperature for 20 hours, quenched with aqueous Na$_2$S$_2$O$_3$ (1.5 mL, 2 M), and then extracted with EtOAc (2.0 mL). The organic layer was analyzed by GC after adding dodecane (10 μL) as internal standard.

TABLE S1

Catalyst screen

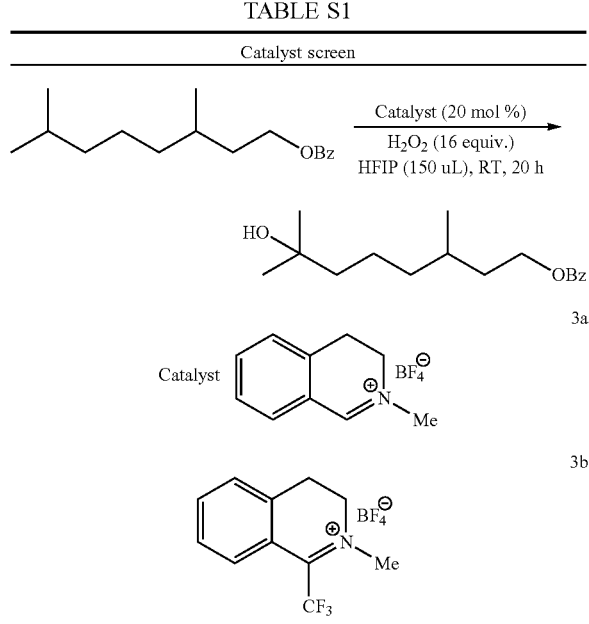

3a

3b

3c

TABLE S1-continued

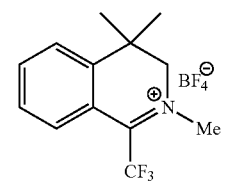

3d

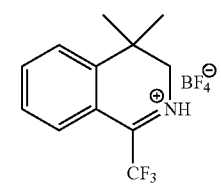

3e

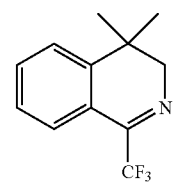 [SMILES: CC1(C)CN=C(C(F)(F)F)c2ccccc21]

| Entry | Catalyst | Conversion (%) | Yield (%) |
| --- | --- | --- | --- |
| 1 | 3a | <1 | <1 |
| 2 | 3b | 12 | 3 |
| 3 | 3c | 70 | 57 |
| 4 | 3d | <1 | <1 |
| 5 | 3e | <1 | <1 |
| 6 | Et$_2$O—HBF$_4$ | <1 | <1 |

1.2 General Procedure for Evaluating Co-Solvent Effect on the Hydroxylation 3,7-Dimethyloctyl benzoate (52.4 mg, 0.2 mmol), 3c (13.2 mg, 0.04 mmol), hexafluoro-2-propanol (150 μL), and 200 μL of co-solvent were mixed in a 5 mL vial equipped with a stirring bar. H$_2$O$_2$ (181 μL, 50 wt. % in H$_2$O, 3.2 mmol) was then added in one portion. The reaction mixture was stirred at room temperature for 20 hours, quenched with aqueous Na$_2$S$_2$O$_3$ (1.5 mL, 2 M), and then extracted with EtOAc (2.0 mL). The organic phase was analyzed by GC after adding dodecane (10 μL) as internal standard.

TABLE S2

Co-solvent effect 3c (20 mol %), H$_2$O$_2$ (16 equiv.), HFIP (150 uL), co-solvent (200 uL), RT, 20 h

| Entry | Co-solvent | Conversion (%) | Yield (%) |
|---|---|---|---|
| 1 | — | 70 | 57 |
| 2 | Dichloroethane | 31 | 21 |
| 3 | EtOAc | <1 | <1 |
| 4 | MeCN | 2 | <1 |

1.3 General Procedure for Evaluating pH Effect on the Hydroxylation

Potassium bisphthalate buffer: 0.05 Molar, pH=4.00; Potassium phosphate monobasic-sodium hydroxide buffer: 0.05 Molar, pH=7.00.

3,7-Dimethyloctyl benzoate (52.4 mg, 0.2 mmol), 3c (13.2 mg, 0.04 mmol), hexafluoro-2-propanol (150 µL), and buffer solution were mixed in a 5 mL vial equipped with a stirring bar. H$_2$O$_2$ (181 µL, 50 wt. % in H$_2$O, 3.2 mmol) was then added in one portion. The reaction mixture was stirred at room temperature for 20 hours, quenched with aqueous Na$_2$S$_2$O$_3$ (1.5 mL, 2 M), and then extracted with EtOAc (2.0 mL). The organic phase was analyzed by GC after adding dodecane (10 µL) as internal standard.

TABLE S3 pH effect 3c (20 mol %), H$_2$O$_2$ (16 equiv.), HFIP (150 uL), Buffer, RT, 20 h

| Entry | Buffer (µL) | Conversion (%) | Yield (%) |
|---|---|---|---|
| 1 | — | 70 | 57 |
| 2 | pH = 4 (200) | 15 | 7 |
| 3* | pH = 4 (500) | 23 | 15 |
| 4 | pH = 7 (200) | 19 | 10 |

*The buffer solution was dried under vacuum and the residue was added to the reaction mixture.

1.4 General Procedure for Evaluating Temperature Effect on the Hydroxylation 3,7-Dimethyloctyl benzoate (52.4 mg, 0.2 mmol), 3c (13.2 mg, 0.04 mmol), and hexafluoro-2-propanol (150 µL) were mixed in a 5 mL vial equipped with a stirring bar. H$_2$O$_2$ (181 µL, 50 wt. % in H$_2$O, 3.2 mmol) was then added in one portion. The reaction mixture was cooled or heated to the designated temperature and stirred for 20 hours then quenched with aqueous Na$_2$S$_2$O$_3$ (1.5 mL, 2 M) and extracted with EtOAc (2.0 mL). The organic phase was analyzed by GC after adding dodecane (10 µL) as internal standard.

TABLE S4

Temperature effect on the hydroxylation 3c (20 mol %), H$_2$O$_2$ (16 equiv.), HFIP (150 uL), T, 20 h

| Entry | T (° C.) | Conversion (%) | Yield (%) |
|---|---|---|---|
| 1 | 4 | 46 | 43 |
| 2 | 22 | 70 | 57 |
| 3 | 30 | 61 | 47 |
| 4 | 50 | 49 | 25 |

1.5 General Procedure for Evaluating the Effect of the Amount of HFIP on the Hydroxylation 3,7-Dimethyloctyl benzoate (52.4 mg, 0.2 mmol), 3c (13.2 mg, 0.04 mmol), and designated amount of hexafluoro-2-propanol were mixed in a 5 mL vial equipped with a stirring bar. H$_2$O$_2$ (181 µL, 50 wt. % in H$_2$O, 3.2 mmol) was then added in one portion. The reaction mixture was stirred at room temperature for 20 hours, quenched with aqueous Na$_2$S$_2$O$_3$ (1.5 mL, 2 M), and then extracted with EtOAc (2.0 mL). The organic phase was analyzed by GC after adding dodecane (10 µL) as internal standard.

TABLE S5

The effect of the amount of HFIP on the hydroxylation 3c (20 mol %), H$_2$O$_2$ (16 equiv.), HFIP (X uL), RT, 20 h

| Entry | HFIP (µL) | Conversion (%) | Yield (%) |
|---|---|---|---|
| 1 | 100 | 59 | 47 |
| 2 | 150 | 70 | 57 |
| 3 | 200 | 74 | 64 |
| 4 | 250 | 68 | 59 |

2. CH Bonds Hydroxylation Under Optimized Conditions

TABLE S6

Hydroxylation of various substrates using optimized conditions.

Reaction scheme: R₃C–H → R₃C–OH using 3c (20 mol %), H₂O₂ (16 equiv.), HFIP, RT, 20 h. Catalyst 3c: 4,4-dimethyl-1-(trifluoromethyl)-2-methyl-3,4-dihydroisoquinolinium tetrafluoroborate.

| Compound Number | Structure | Isolated yield (%) | Recovered Starting Material (%) |
|---|---|---|---|
| 2 | HO–C(Me)₂–CH₂CH₂CH₂–CH(Me)–CH₂CH₂–OBz | 56 | 33 |
| 4 | HO–C(Me)₂–CH₂CH₂CH₂–CH(Me)–CH₂CH₂–OAc | 63 | 21 |
| 5 | HO–C(Me)₂–CH₂CH₂CH₂–CH(Me)–OAc | 46 | 32 |
| 6 | HO–C(Me)₂–CH₂CH₂CH₂–CH(Me)–NHCOCF₃ | 50 | 49 |
| 7 | HO–C(Me)₂–CH₂CH₂CH₂–OBz | 33 | 63 |
| 8 | HO–C(Me)₂–CH₂CH₂CH₂CH₂–CH(Me)–CH₂–C(O)–C₆H₄–Cl | 42 | 49 |
| 9[a] | trans-1-Me-1-HO-4-OPiv-cyclohexane | 39 | 46 |
| 10 | HO–C(Me)₂–CH₂CH₂CH₂CH₂–CH(Me)–CH₂CH₂–N(phthalimide) | 54 | 30 |
| 11[b] | 3α-AcO-5β-hydroxy-cholan-24-oic acid methyl ester | 36 | 39 |
| 12 | HO–C(Me)₂–CH₂CH₂CH₂CH₂–CH(Me)–CH₂CH₂–OH | 56 | 7 |

TABLE S6-continued

Hydroxylation of various substrates using optimized conditions.

| Compound Number | Structure | Isolated yield (%) | Recovered Starting Material (%) |
|---|---|---|---|
| 13 | HO-C(Me)2-CH2-CH2-CH(Me)-CH2-CH2-C(Me)(Et)-OH | 58 | 33 |
| 14 | HO-C(Me)2-CH2-CH2-CH(Me)-CH2-CH2-O-Me | 45 | 48 |
| 15 | HO-C(Me)2-CH2-CH2-CH2-OH | 25 | 63 |
| 16 | HO-C(Me)2-CH2-CH2-CH2-CH(Me)-OH | 42 | 41 |
| 16[c] | HO-C(Me)2-CH2-CH2-CH2-CH(Me)-OH | 16 | 68 |
| 17[d] | cholestane-3β,25-diol structure | 20 | 47 |

[a] Reaction was performed on 0.2 mmol scale and 40 mol % catalyst was used.
[b] Reaction was performed on 0.2 mmol scale and catalyst/$H_2O_2$ was added in two portions ($2^{nd}$ addition at 24 hours).
[c] Reaction was performed on 0.2 mmol scale and 200 μL of dichloromethane was used for comparison with Entry 14. 6-Methyl-2-heptanone was observed in 13% yield. The GC yield was reported.
[d] Reaction was performed on 0.2 mmol scale and 200 μL of dichloromethane was used for better solubility of substrate.

General Procedure for Hydroxylation:

Except where noted above, substrate (0.4 mmol), iminium 3c (26.4 mg, 0.08 mmol), and hexafluoro-2-propanol (400 μL) were mixed in a 5 mL vial equipped with a stir bar. $H_2O_2$ (362 μL, 50 wt. % in water, 6.4 mmol) was then added in one portion and the resulting mixture was stirred at room temperature overnight (20 hours). The mixture was then carefully quenched with 2M aqueous $Na_2S_2O_3$ (3 mL) and extracted with EtOAc (4×3 mL). The combined organic extracts were dried over $MgSO_4$, filtered, and concentrated under vacuum. The residue was purified by chromatography on silica gel to give product and recovered starting material.

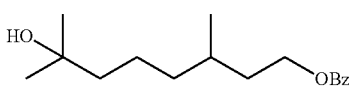

Product 2: Starting material: 3,7-dimethyloctyl benzoate (104.8 mg, 0.4 mmol). Purified by chromatography (silica gel, hexanes/EtOAc 25/1 to 5/1). Product: 62.2 mg of clear oil, 0.22 mmol, 56%. Recovered starting material: 34.7 mg, 0.13 mmol, 33%. $^1$H NMR (600 MHz, CDCl$_3$): δ 8.03 (dd, J=8.3, 1.3 Hz, 2H), 7.54 (tt, J=7.5, 1.3 Hz, 1H), 7.42 (t, J=7.8 Hz, 2H), 4.39-4.31 (m, 2H), 1.81 (m, 1H), 1.69-1.62 (m, 1H), 1.57 (m, 1H), 1.46-1.29 (m, 6H), 1.20 (s, 6H), 0.96 (d, J=6.6 Hz, 3H) ppm; $^{13}$C NMR (150 MHz CDCl$_3$): δ 166.7, 132.8, 130.4, 129.5, 128.3, 71.2, 63.5, 44.0, 37.4, 35.5, 30.0, 29.2, 29.2, 21.6, 19.6 ppm. NMR spectra are consistent with literature reports.[12]

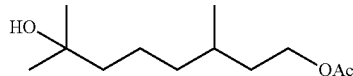

Product 4: Starting material: 3,7-dimethyloctyl acetate (80.0 mg, 0.4 mmol). Purified by chromatography (silica gel, hexanes/EtOAc 25/1 to 4/1). Product: 54.9 mg of clear oil, 0.25 mmol, 63%. Recovered starting material: 16.8 mg, 0.08 mmol, 21%. $^1$H NMR (600 MHz, CDCl$_3$): δ 4.12-4.03 (m, 2H), 2.02 (s, 3H), 1.64 (m, 1H), 1.53 (m, 1H), 1.47-1.25 (m, 6H), 1.19 (s, 6H), 1.15 (m, 1H), 0.89 (d, J=6.6 Hz, 3H) ppm; $^{13}$C NMR (150 MHz CDCl$_3$): δ 171.2, 71.0, 63.0, 44.1, 37.3, 35.4, 29.8, 29.3, 29.2, 21.6, 21.0, 19.4 ppm. NMR spectra are consistent with literature reports.[13]

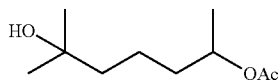

Product 5: Starting material: 6-methylheptan-2-yl acetate (68.9 mg, 0.4 mmol). Purified by chromatography (silica gel, hexanes/EtOAc 25/1 to 4/1). Product: 34.5 mg of clear oil, 0.18 mmol, 46%. Recovered starting material: 22.3 mg, 0.13 mmol, 32%. $^1$H NMR (600 MHz, CDCl$_3$): δ 4.89 (m, 1H), 2.00 (s, 3H), 1.61-1.55 (m, 1H), 1.48-1.30 (m, 5H), 1.19 (d, J=6.3 Hz, 3H), 1.18 (s, 6H) ppm; $^{13}$C NMR (150 MHz CDCl$_3$): δ 170.8, 70.82, 70.80, 43.5, 36.3, 29.2, 29.1, 21.4, 20.1, 20.0 ppm. NMR spectra are consistent with literature reports. [13]

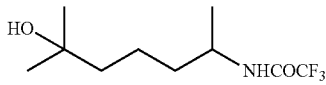

Product 6: Starting material: 2,2,2-trifluoro-N-(6-methylheptan-2-yl)acetamide (90.1 mg, 0.4 mmol). Purified by chromatography (silica gel, hexanes/EtOAc 4/1). Product: 48.6 mg of viscous oil, 0.2 mmol, 50%. Recovered starting material: 44.3 mg, 0.196 mmol, 49%. $^1$H NMR (600 MHz, CDCl$_3$): δ 6.34 (br s, 1H), 4.02 (m, 1H), 1.56-1.36 (m, 6H), 1.21 (d, J=6.6 Hz, 3H), 1.18 (s, 6H) ppm; $^{13}$C NMR (150 MHz CDCl$_3$): δ 156.59 (q, J=36 Hz), 115.9 (q, J=288 Hz), 70.8, 46.4, 43.0, 36.6, 29.3, 29.2, 20.5, 20.3 ppm; $^{19}$F NMR (564 MHz CDCl$_3$): δ −76.87 ppm. NMR spectra are consistent with literature reports.[13]

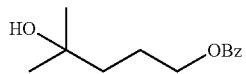

Product 7: Starting material: 4-methylpentyl benzoate (82.5 mg, 0.4 mmol). Purified by chromatography (silica gel, hexanes/EtOAc 25/1 to 4/1). Product: 24.9 mg of viscous oil, 0.11 mmol, 28%. Recovered starting material: 53.0 mg, 0.26 mmol, 64%. $^1$H NMR (600 MHz, CDCl$_3$): δ 8.02 (dd, J=8.4, 1.3 Hz, 2H), 7.54 (tt, J=7.4, 1.3 Hz, 1H), 7.42 (dd, J=8.4, 7.4 Hz, 2H), 4.33 (t, J=6.6 Hz, 2H), 1.88-1.83 (m, 2H), 1.61-1.58 (m, 2H), 1.24 (s, 6H) ppm; $^{13}$C NMR (150 MHz CDCl$_3$): δ 166.6, 132.9, 130.3, 129.5, 128.3, 70.7, 65.3, 40.0, 29.3, 23.9 ppm. NMR spectra are consistent with literature reports. [12]

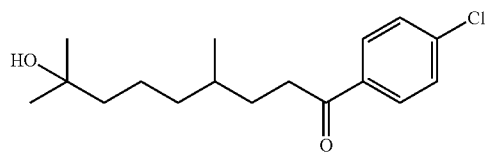 [SMILES: CC(CCCC(C)(C)O)CCC(=O)c1ccc(Cl)cc1]

Product 8: Starting material: 4,8-dimethyl-1-(4-chlorophenyl)-1-nonanone (112.0 mg, 0.4 mmol). Purified by chromatography (silica gel, hexanes/EtOAc 25/1 to 5/1). Product: 50.3 mg of viscous oil, 0.17 mmol, 42%. Recovered starting material: 55.2 mg, 0.2 mmol, 49%. $^1$H NMR (600 MHz, CDCl$_3$): δ 7.87 (d, J=8.6 Hz, 2H), 7.41 (d, J=8.6 Hz, 2H), 2.97-2.86 (m, 2H), 1.78-1.73 (m, 1H), 1.54-1.28 (m, 7H), 1.19 (s, 9H), 1.17-1.14 (m, 1H), 0.91 (d, J=6.4 Hz, 3H) ppm; $^{13}$C NMR (150 MHz CDCl$_3$): δ 199.5, 139.3, 135.3, 129.5, 128.8, 71.1, 44.1, 37.3, 36.3, 32.5, 31.2, 29.3, 29.1, 21.7, 19.5 ppm; IR (film, cm$^{-1}$): 3421 (br), 2935, 1682, 1589, 1378, 1271, 1205, 1092, 1013, 908, 835, 731; HRMS m/z (ESI$^+$): Calculated for $C_{17}H_{25}ClNaO_2$ [M+Na]$^+$: 319.1441, found 319.1429.

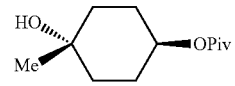

Product 9: Starting material: 6-methyl-2-heptanol (39.6 mg, 0.2 mmol). Purified by chromatography (silica gel, hexanes/EtOAc 4/1). Product: 16.6 mg of viscous oil, 0.077 mmol, 39%. Recovered starting material: 18.4 mg, 0.093 mmol, 46%. $^1$H NMR (600 MHz, CDCl$_3$): δ 4.90 (m, 1H), 1.89-1.83 (m, 2H), 1.69-1.60 (m, 4H), 1.51-1.47 (m, 2H), 1.25 (s, 3H), 1.17 (s, 9H) ppm; $^{13}$C NMR (150 MHz CDCl$_3$): δ 177.9, 69.3, 69.2, 38.9, 34.4, 30.2, 27.2, 26.3 ppm. NMR spectra are consistent with literature reports.[13]

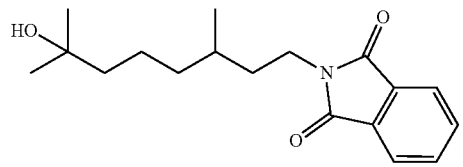 [SMILES: CC(CCCC(C)(C)O)CCN1C(=O)c2ccccc2C1=O]

Product 10: Starting material: 2-(3,7-dimethyloctyl) isoindoline-1,3-dione (115.0 mg, 0.4 mmol). Purified by chromatography (silica gel, hexanes/EtOAc 4/1). Product: 65.0 mg of viscous oil, 0.21 mmol, 54%. Recovered starting material: 34.2 mg, 0.12 mmol, 30%. 1H NMR (600 MHz, CDCl$_3$): δ 7.82 (dd, J=5.5, 3.0 Hz, 2H), 7.69 (dd, J=5.5, 3.0 Hz, 2H), 3.69 (m, 2H), 1.69 (q, J=8.0 Hz, 1H), 1.49-1.29 (m, 8H), 1.19 (s, 6H), 0.96 (d, J=6.5 Hz, 3H) ppm; $^{13}$C NMR (150 MHz CDCl$_3$): δ 168.4, 133.8, 132.1, 123.1, 71.1, 44.0, 37.1, 36.2, 35.3, 30.6, 29.2, 29.1, 21.4, 19.4 ppm. NMR spectra are consistent with literature reports. [8]

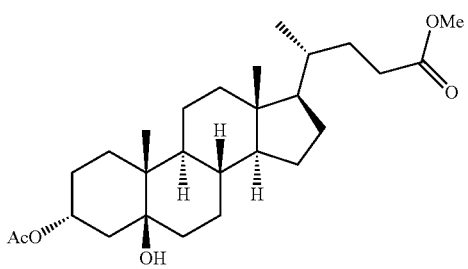

Product 11: Starting material: methyl 3α-acetoxy-5β-cholan-24-oate (86.1 mg, 0.2 mmol). Purified by chromatography (silica gel, hexanes/EtOAc 10/1 to 3/1). Product: 32.7 mg of white solid, 0.073 mmol, 36%. Recovered starting material: 33.7 mg, 0.078 mmol, 39%. $^1$H NMR (600 MHz, CDCl$_3$): δ 5.08 (tt, J=11.5, 5.0 Hz, 1H), 3.66 (s, 3H), 2.39-2.31 (m, 1H), 2.26-2.17 (m, 1H), 2.15-2.07 (m, 1H), 2.02 (s, 3H), 1.98 (d, J=12.6 Hz, 1H), 1.90-1.63 (m, 6H), 1.58 (dt, J=26.7, 14.4 Hz, 6H), 1.45-1.34 (m, 8H), 1.34-1.25 (m, 4H), 1.23 (d, J=29.0 Hz, 1H), 1.17-0.99 (m, 7H), 0.92-0.89 (m, 6H), 0.64 (s, 3H) ppm; $^{13}$C NMR (151 MHz, CDCl$_3$) δ 174.7, 170.5, 75.4, 71.4, 56.5, 55.8, 51.5, 43.2, 42.5, 39.8, 39.7, 38.2, 36.9, 35.3, 34.9, 31.1, 31.0, 29.4, 28.6, 28.1, 26.2, 24.2, 21.4, 21.1, 18.2, 16.3, 12.0 ppm; IR (film, cm$^{-1}$): 3486 (br), 2939 (m), 2869 (w), 1738 (s), 1249 (m). NMR spectra are consistent with literature reports.[14]

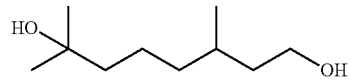

Product 12: Starting material: 3,7-dimethyl-1-octanol (63.3 mg, 0.4 mmol). Purified by chromatography (silica gel, hexanes/EtOAc 4/1 to 1/4). Product: 38.9 mg of clear oil, 0.22 mmol, 56%. Recovered starting material: 4.4 mg, 0.028 mmol, 7%. $^1$H NMR (600 MHz, CDCl$_3$): δ 3.70-3.61 (m, 2H), 1.62-1.54 (m, 2H), 1.45-1.27 (m, 6H), 1.19 (s, 6H), 1.16-1.12 (m, 1H), 0.88 (d, J=6.6 Hz, 3H) ppm; $^{13}$C NMR (151 MHz, CDCl$_3$): δ 71.0, 61.1, 44.0, 39.8, 37.51, 29.4, 29.3, 29.2, 21.6, 19.6 ppm. NMR spectra are consistent with literature reports.[5]

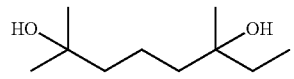

Product 13: Starting material: 3,7-dimethyl-3-octanol (63.3 mg, 0.4 mmol). Purified by chromatography (silica gel, hexanes/EtOAc 5/1 to 1/2). Product: 40.5 mg of viscous oil, 0.23 mmol, 58%. Recovered starting material: 20.8 mg, 0.13 mmol, 33%. $^1$H NMR (600 MHz, CDCl$_3$): δ 1.50-1.37 (m, 8H), 1.19 (s, 6H), 1.13 (s, 3H), 0.87 (t, J=7.5 Hz, 3H) ppm; $^{13}$C NMR (151 MHz, CDCl$_3$): δ 72.9, 71.0, 44.3, 41.7, 34.3, 29.27, 29.26, 26.3, 18.5, 8.20 ppm. NMR spectra are consistent with literature reports [13].

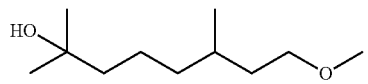

Product 14: Starting material: 1-methoxy-3,7-dimethyloctane (69.0 mg, 0.4 mmol). Purified by chromatography (silica gel, pentane/Et$_2$O 4/1 to 2/1). Product: 34.1 mg of clear oil, 0.18 mmol, 45%. Recovered starting material: 32.8 mg, 0.19 mmol, 48%. $^1$H NMR (600 MHz, CDCl$_3$): δ 3.38 (td, J=6.9, 5.2 Hz, 2H), 3.31 (s, 3H), 1.63-1.51 (m, 2H), 1.45-1.26 (m, 6H), 1.19 (s, 6H), 1.17-1.08 (m, 1H), 0.87 (d, J=6.7 Hz, 3H) ppm; $^{13}$C NMR (151 MHz, CDCl$_3$): δ 71.11, 71.06, 58.5, 44.1, 37.6, 36.6, 29.8, 29.3, 29.1, 21.6, 19.6 ppm. NMR spectra are consistent with literature reports.[10]

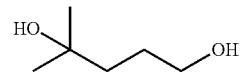

Product 15: Starting material: 4-methyl-1-pentanol (40.8 mg, 0.4 mmol). Purified by chromatography (silica gel, hexanes/EtOAc 20/1 to 1/5). Product: 11.6 mg of viscous oil, 0.01 mmol, 25%. Recovered starting material: 25.7 mg, 0.25 mmol, 63%. $^1$H NMR (600 MHz, CDCl$_3$): δ 3.66 (t, J=6.0 Hz, 2H), 2.14 (br, 2H), 1.67 (m, 2H), 1.60-1.55 (m, 2H), 1.23 (s, 6H) ppm; $^{13}$C NMR (151 MHz, CDCl$_3$): δ 70.7, 63.3, 40.4, 29.4, 27.4 ppm. NMR spectra are consistent with literature reports.[16]

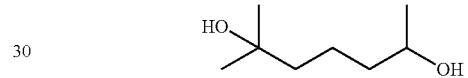

Product 16: Starting material: 6-methyl-2-heptanol (52.1 mg, 0.4 mmol). Purified by chromatography (silica gel, hexanes/EtOAc 20/1 to 1/5). Product: 24.7 mg of viscous oil, 0.17 mmol, 42%. Recovered starting material: 21.4 mg, 0.16 mmol, 41%. $^1$H NMR (600 MHz, CDCl$_3$): δ 3.84-3.78 (m, 1H), 1.50-1.37 (m, 6H), 1.20 (s, 6H), 1.18 (d, J=6.1 Hz, 3H) ppm; $^{13}$C NMR (151 MHz, CDCl$_3$): δ 71.0, 68.0, 43.6, 39.6, 29.3, 29.2, 23.6, 20.5 ppm. NMR spectra are consistent with literature reports.[17]

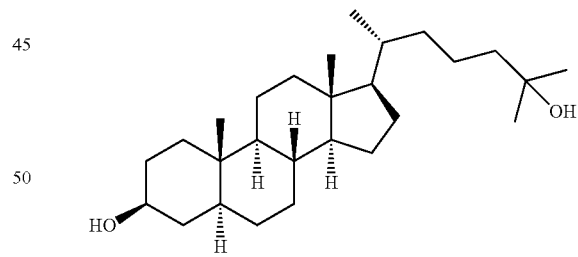

Product 17: Starting material: (+)-dihydrocholesterol (77.7 mg, 0.2 mmol). Purified by chromatography (silica gel, hexanes/EtOAc/DCM 10/3/3). Product: 16.0 mg of white solid, 0.04 mmol, 20%. Recovered starting material: 36.8 mg, 0.095 mmol, 47%. $^1$H NMR (600 MHz, CDCl$_3$): δ 3.57 (m, 1H), 1.95 (dt, J=12.6, 3.5 Hz, 1H), 1.81-1.75 (m, 2H), 1.69 (dt, J=13.3, 3.6 Hz, 1H), 1.64 (dq, J=12.9, 3.5 Hz, 1H), 1.57-1.22 (m, 18H), 1.20 (s, 6H), 1.12-0.94 (m, 7H), 0.90 (d, J=6.5 Hz, 3H), 0.85 (dt, J=10.7, 6.1 Hz, 1H), 0.79 (s, 3H), 0.63 (s, 3H), 0.62-0.58 (m, 1H) ppm; $^{13}$C NMR (151 MHz, CDCl$_3$): δ 71.4, 71.2, 56.5, 56.2, 54.3, 44.8, 44.4, 42.6, 40.0, 38.2, 37.0, 36.4, 35.7, 35.5, 35.4, 32.1, 31.5, 29.3, 29.2, 28.7, 28.2, 24.2, 21.2, 20.8, 18.6, 12.3, 12.1 ppm; IR (film, cm$^{-1}$):

3294 (br), 2931, 2863, 1468, 1379, 1156, 1041, 911. LRMS (ESI) Calculated for $C_{27}H_{45}$ $[M+H-2H_2O]^+$: 369.4, found 369.4. $[\alpha]^{22}_D$=+24.5° (c=0.5, $CH_3OH$).

Hydroxylation of Cyclohexane Catalyzed by Iminium 3c

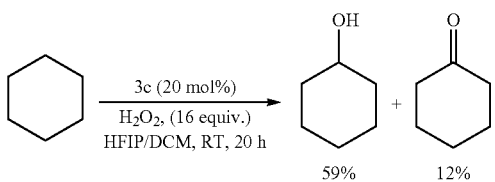

Figure 6:
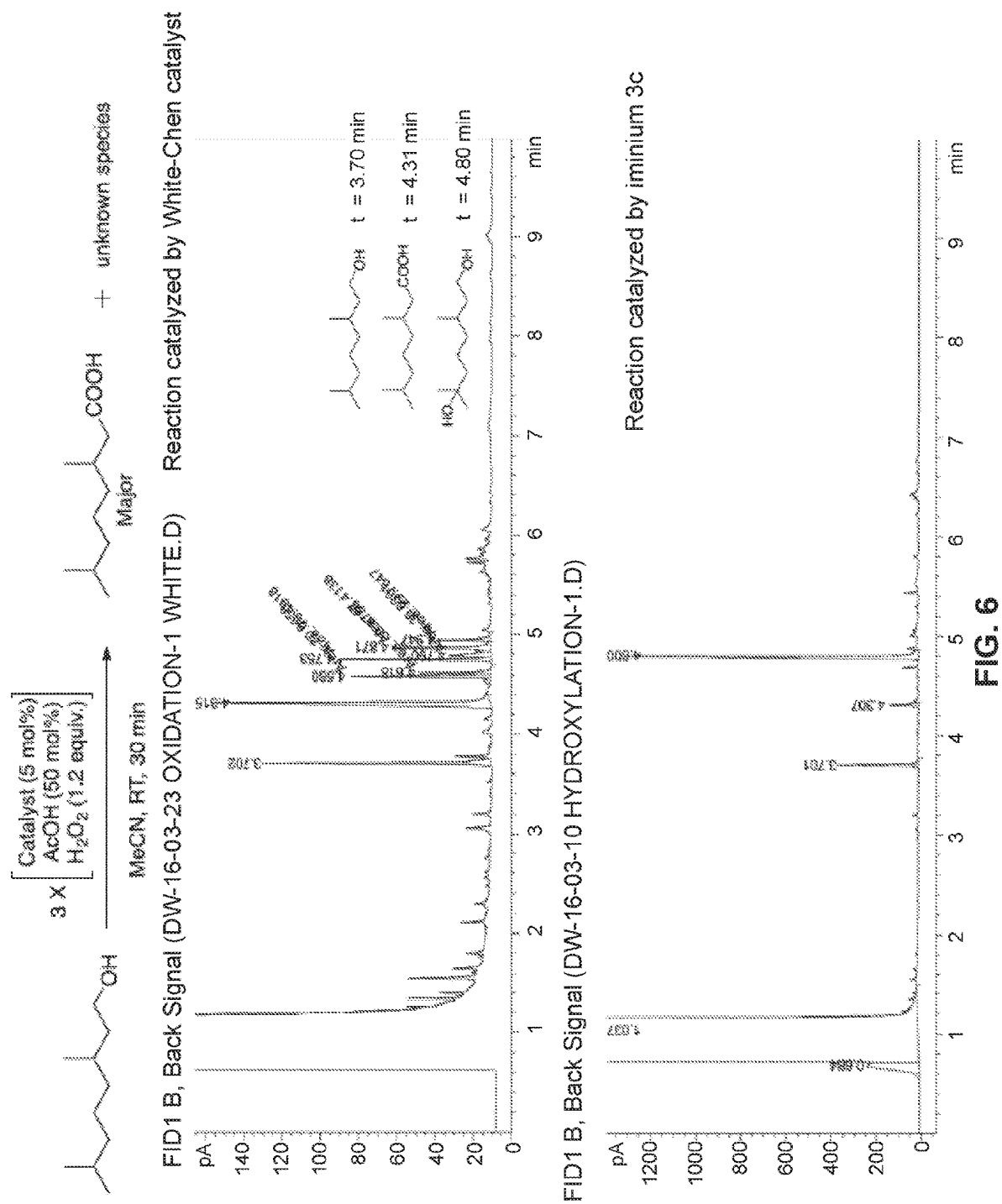
FIG. 6 illustrates the hydroxylation of 3,7-dimethyl-1-octanol catalyzed by White-Chen catalyst or iminium 3c.

Cyclohexane (16.8 mg, 0.2 mmol), 3c (13.2 mg, 0.04 mmol), HFIP (200 μL), and DCM (100 μL) were mixed in a 5 mL vial equipped with a stir bar. $H_2O_2$ (181 μL, 50 wt. % in $H_2O$, 3.2 mmol) was then added in one portion. The reaction mixture was stirred at room temperature for 20 hours, quenched with aqueous $Na_2S_2O_3$ (1.5 mL, 2 M), and then extracted with EtOAc (2.0 mL). The organic phase was analyzed by GC after adding dodecane (50 μL) as internal standard. GC yield was corrected according to the burn ratios of cyclohexanol and cyclohexanone to dodecane. As shown in FIG. 6, the reaction produced cyclohexanol in 59% yield and cyclohexanone in 12% yield.

3. Comparison of Selectivity of Iminium Catalyst and White-Chen Catalyst for Hydroxylation Hydroxylation of 3,7-dimethyl-1-octanol, 6-methyl-2-heptanol, and 3,7-dimethyloctyl acetate was performed by following White's procedure [13]. The result was compared with that obtained by using iminium catalyst 3c (FIG. 6).

General Procedure for Hydroxylation Using White-Chen Catalyst:

A 10 mL vial was charged with the following: Fe(S,S-PDP)[18] (9.3 mg, 0.01 mmol, 5 mol %), substrate (0.20 mmol, 1.0 equiv.), MeCN (0.3 mL), and AcOH (6.0 mg, 0.10 mmol, 50 mol %) and a magnetic stir bar. The vial was placed on a stir plate and stirred vigorously at room temperature. A solution of $H_2O_2$ (50 wt. % in $H_2O$, 14.7 μL, 0.24 mmol, 1.2 equiv.) in MeCN (1.8 mL) was added dropwise via syringe over ca. 45 seconds. After ca. 10 minutes, a solution of Fe(S,S-PDP) (9.3 mg, 0.01 mmol, 5 mol %), AcOH (6.0 mg, 0.10 mmol, 50 mol %), in MeCN (0.2 mL) was added via pipette. This was followed by $H_2O_2$ (50 wt. % in $H_2O$, 14.7 μL, 0.24 mmol, 1.2 equiv.) in MeCN (1.8 mL) added dropwise over ca. 45 seconds. A third addition was done in the same manner for a total of 15 mol %, 1.5 equiv. AcOH, and 3.6 equiv. $H_2O_2$. Each addition was allowed to stir for 10 minutes, for a total reaction time of 30 minutes.

Figure 7:
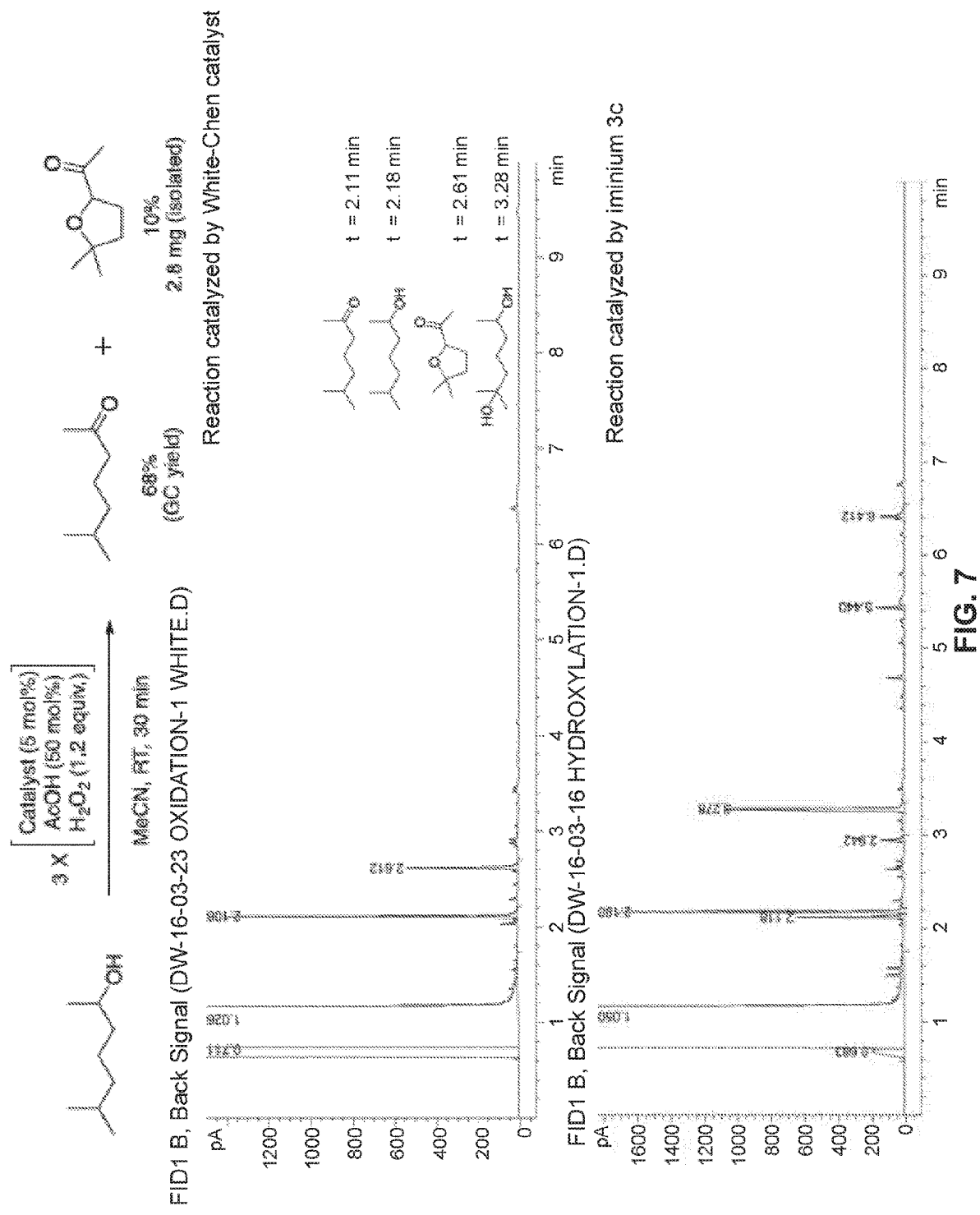
FIG. 7 illustrates the hydroxylation of 6-methyl-2-heptanol catalyzed by White-Chen or iminium 3c.

3,7-dimethyl-1-octanol (31.7 mg, 0.2 mmol). The crude mixture was rotovapped down to a minimal amount of MeCN. Et2O was added until a brown precipitate formed. The mixture was filtered through a short plug of celite and the filtrate was analyzed by GC. As shown in FIG. 7, the reaction produced 3,7-dimethyl-1-caprylic acid as major product in 60% yield, which was confirmed by GC-MS and $^1$HNMR analysis of crude product.

6-Methyl-2-heptanol (26.0 mg, 0.2 mmol). The reaction was quenched with a solution of saturated $NaHCO_3$. The aqueous layer was extracted with Et2O (3×10 mL) and the organic layers were combined, dried over MgSO4, and filtered. The filtrate was analyzed by GC before concentrated carefully by rotary evaporation. As shown in Figure S3, starting material was consumed completely and 6-methyl-2-heptanone was produced as major product in 68% GC yield, which was confirmed by comparing with authentic sample. The residue was separated by flash chromatography to give 5-acetyl-2,2-dimethyltetrahydrofuran as the second product (2.8 mg, 10%). 1H NMR (600 MHz, CDCl3): δ 4.28 (s, 1H), 2.30-2.25 (m, 4H), 2.16-2.10 (m, 1H), 2.06-2.02 (m, 1H), 1.97-1.90 (m, 1H), 1.43 (s, 3H), 1.31 (s, 3H) ppm; 13C NMR (151 MHz, CDCl3): δ 206.4, 104.3, 84.7, 37.7, 36.0, 29.4, 28.2, 22.7 ppm. NMR spectra are consistent with literature reports. [19]

Figure 8:
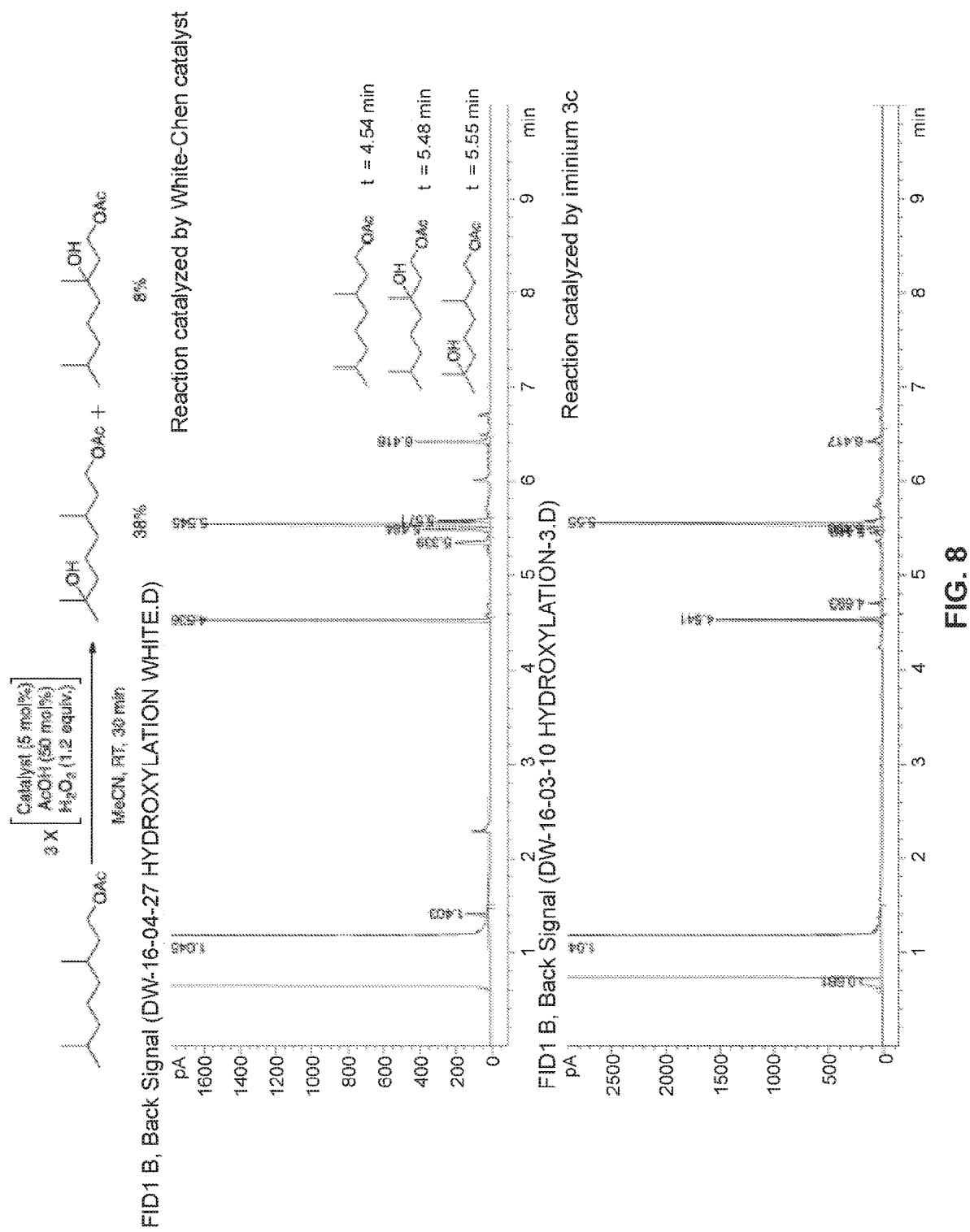
FIG. 8 illustrates the hydroxylation of 3,7-dimethyl acetate catalyzed by White-Chen or iminium 3c.

3,7-dimethyloctyl acetate (40.1 mg, 0.2 mmol). The crude mixture was rotovapped down to a minimal amount of MeCN. Et2O was added until a brown precipitate formed. The mixture was filtered through a short plug of celite and the filtrate was analyzed by GC (FIG. 8). After concentrated under vacuum, the residue was purified by flash chromatography (silica, hexanes/EtOAc 5/1) to give 7-hydroxy-3,7-dimethyloctyl acetate (16.3 mg, 38%) and 3-hydroxy-3,7-dimethyloctyl acetate (3.4 mg, 8%). 3-Hydroxy-3,7-dimethyloctyl acetate: 1H NMR (600 MHz, CDCl3): δ 4.22 (t, J=7.0 Hz, 2H), 2.04 (s, 3H), 1.80 (m, 2H), 1.53 (m, 1H), 1.46-1.42 (m, 2H), 1.35-1.29 (m, 2H), 1.20 (s, 3H), 1.18-1.14 (m, 2H), 0.86 (d, J=6.6 Hz, 6H); 13C NMR (151 MHz, CDCl3): δ 171.0, 71.9, 61.3, 42.8, 39.6, 39.4, 27.9, 27.0, 22.6, 21.7, 21.1 NMR spectra are consistent with literature reports. [13]

4. Preliminary Mechanism Investigation

To rule out free radical reaction pathway, iminium-catalyzed hydroxylation of 3,7-dimethyloctyl benzoate was performed in dark or in presence of butylated hydroxytoluene (BHT). 3,7-Dimethyloctyl benzoate (52.4 mg, 0.2 mmol), 3c (13.2 mg, 0.04 mmol), and hexafluoro-2-propanol (200 μL) were mixed in a 5 mL vial (for reaction in dark, the vial was wrapped with foil and the fume hood light was left off) with a stirring bar followed by the addition of H2O2 (181 μL, 50 wt. % in H2O, 3.2 mmol) (for reaction with BHT, 4.4 mg of BHT was introduced before the addition of H2O2). The reaction mixture was stirred at room temperature for 20 hours, quenched with aqueous Na2S2O3 (1.5 mL, 2 M), and then extracted with EtOAc (2.0 mL). The organic phase was analyzed by GC after addition of dodecane (10 μL) as internal standard. The results were shown in Table S7.

TABLE S7

Hydroxylation of 3,7-dimethyloctyl benzoate in dark or in presence of BHT.

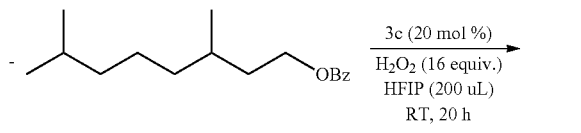

| Entry | Condition | Conversion (%) | Yield (%) |
|---|---|---|---|
| 1 | Standard (control) | 74 | 64 |
| 2 | In dark | 77 | 63 |
| 3 | BHT (10 mol %) | 74 | 61 |

The disclosures of each and every patent, patent application, and publication cited herein are hereby incorporated by reference herein in their entirety.

Headings are included herein for reference and to aid in locating certain sections. These headings are not intended to limit the scope of the concepts described therein under, and these concepts may have applicability in other sections throughout the entire specification.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an aspect, the term "about" can include traditional rounding according to significant figures of the numerical value. In addition, the phrase "about 'x' to 'y'" includes "about 'x' to about 'y'" Many variations and modifications may be made to the above-described aspects. All such modifications and variations are intended to be included herein within the scope of this disclosure and protected by the following claims.

I claim:

1. A composition, comprising: an iminium catalyst having the following structure:

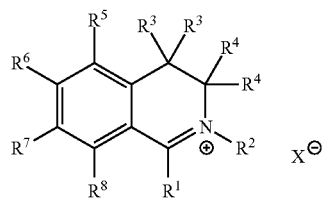

wherein $R^1$ is —$CF_3$;

wherein $R^2$ is selected from the group consisting of: —$CH_3$, -Ph, —$CF_5$, —$CF_3$, —$CH_2Ph$, -cyclohexyl, -adamantyl, -cyclopropyl, —CnHn+$_2$, CnFn+$_2$, biphenyl, substituted biphenyl, alkyl, substituted alkyl, perfluoroalkyl, aryl, perfluroraryl, substituted aryl, and glycosyl;

wherein each $R^3$ is independently selected from the group consisting of: —$CH_3$, —$CH_2CH_2$—, -Ph, —$CH_2Ph$, $COCH_3$, —$CO_2CH_3$, —$C_nH_{n+2}$, —$C_nF_{n+2}$, cycloalkyl, substituted cycloalkyl, aryl, and perfluoroaryl;

wherein each $R^4$ is independently selected from the group consisting of: —$CH_3$, —$CH_2CH_2$-, —F, —$CF_3$, alkyl, substituted alkyl, perfluoroalkyl, cycloalkyl, substituted cycloalkyl, and perfluorocycloalkyl;

wherein $R^5$ is selected from the group consisting of: —H, —F, —Cl, —Br, —I, $CF_3$, —$C_6F_5$, —$NO_2$, —$OCH_3$, Ph, -p-$C_6H_4NO_2$, —OH, and alkyl;

wherein $R^6$ is selected from the group consisting of: —H, —F, —Cl, —Br, —I, $CF_3$, —$C_6F_5$, —$NO_2$, —$OCH_3$, Ph, -p-$C_6H_4NO_2$, —OH, and alkyl;

wherein $R^7$ is selected from the group consisting of: —H, —F, —Cl, —Br, —I, $CF_3$, —$C_6F_5$, —$NO_2$, —$OCH_3$, Ph, -p-$C_6H_4NO_2$, —OH, and alkyl;

wherein $R^8$ is selected from the group consisting of: —H, —F, —Cl, —Br, —I, $CF_3$, —$C_6F_5$, —$NO_2$, —$OCH_3$, Ph, -p-$C_6H_4NO_2$, $CH_2Ph$, -t-Bu, i-Pr, —OH, and alkyl;

and wherein X is selected from the group consisting of: —$BF_4^-$, —$BPh_4^-$, $SbF_6^-$, $PF_6^-$, $ClO_4^-$, —$CF_3CO_2^-$, $CH_3SO_3^-$, $F^-$, $Cl^-$, $Br^-$, $I^-$, tetrakis(3,5-bis(trifluoromethyl)phenyl)borate.

2. The composition of claim 1, wherein one of the two $R^3$ groups is $R^{3a}$ and the other is $R^{3b}$, and $R^{3a}$ is the same as $R^{3b}$ or different.

3. The composition of claim 1, wherein one of the two $R^4$ groups is $R^{4a}$ and the other is $R^{4b}$, and $R^{4a}$ is the same as $R^{4b}$ or different.

4. The composition of claim 1 wherein each of $R^6$ and $R^7$ are H.

5. A composition of comprising: an iminium catalyst having the following structure:

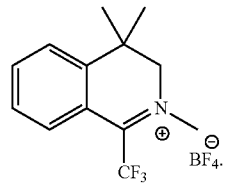

* * * * *